US011754547B2

(12) United States Patent
Ruiz et al.

(10) Patent No.: US 11,754,547 B2
(45) Date of Patent: Sep. 12, 2023

(54) BIORECOGNITION ELEMENTS FOR DETECTION OF FUNGI AND BACTERIA IN FUEL SYSTEMS

(71) Applicant: Government of the United States, as represented by the Secretary of the Air Force, Wright-Patterson AFB, OH (US)

(72) Inventors: Oscar N. Ruiz, Bellbrook, OH (US); Thusitha S Gunasekera, Beavercreek, OH (US); Osman Radwan, Urbana, IL (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 99 days.

(21) Appl. No.: 17/323,205

(22) Filed: May 18, 2021

(65) Prior Publication Data
US 2021/0364491 A1 Nov. 25, 2021

Related U.S. Application Data

(60) Provisional application No. 63/186,844, filed on May 11, 2021, provisional application No. 63/026,853, filed on May 19, 2020.

(51) Int. Cl.
| | |
|---|---|
| *C07K 7/06* | (2006.01) |
| *G01N 33/28* | (2006.01) |
| *G01N 33/569* | (2006.01) |
| *G01N 21/64* | (2006.01) |
| *C07K 17/14* | (2006.01) |

(52) U.S. Cl.
CPC .......... *G01N 33/2835* (2013.01); *C07K 7/06* (2013.01); *C07K 17/14* (2013.01); *G01N 21/6458* (2013.01); *G01N 33/56911* (2013.01); *G01N 33/56961* (2013.01)

(58) Field of Classification Search
None
See application file for complete search history.

(56) References Cited

U.S. PATENT DOCUMENTS

| | | | |
|---|---|---|---|
| 5,369,011 | A | 11/1994 | Embersole et al. |
| 6,747,137 | B1 | 6/2004 | Welnstok et al. |
| 10,295,537 | B2 | 5/2019 | Ruiz et al. |
| 2003/0233675 | A1 | 12/2003 | Cao |
| 2007/0020281 | A1 | 1/2007 | Kearney |
| 2007/0281302 | A1 | 12/2007 | Turnbough |
| 2009/0087878 | A9* | 4/2009 | La Rosa .............. C07K 14/415 800/278 |
| 2009/0300802 | A1 | 12/2009 | Ryan |
| 2011/0214205 | A1 | 9/2011 | Dietrich |
| 2012/0156134 | A1 | 6/2012 | Squires |
| 2014/0352202 | A1 | 12/2014 | Ruiz |
| 2017/0260467 | A1 | 9/2017 | Ruiz |

FOREIGN PATENT DOCUMENTS

WO 2016138245 A2 9/2016

OTHER PUBLICATIONS

I. Chen et al., "Phage display evolution of a peptide substrate for yeast biotin ligase and application to two-color quantum dot labeling of cell surface proteins," JACS, vol. 129 (2007) 6619-6625.
R. Edgar et al., "High-sensitivity bacterial detection using biotin-tagged phage and quantum dot nanocomplexes," PNAS, vol. 103 (2006) 4841-4845.
J. X. Huang et al., "Development of anti-infectives using phage display: biological agents against bacteria, viruses, and parasites," Antimicrob. Agents Chemother., vol. 56 (2012) 4569-4582.
M. A. Walling et al., "Quantum dots for live cell and in vivo imaging," Ing. J. Mol. Sci., vol. 10 (2009) 441-491.
T. S. Gunasekera et al., "Transcriptional profiling suggests that multiple metabolic adaptations are required for effective proliferation of Pseudomonas aeruginosa in jet fuel," Environ. Sci. & Tech., vol. 47 (2013) 13449-13458.
R. C. Striebich et al., "Characterization of the F-76 diesel and Jet-A aviation fuel hydrocarbon degradation profiles of pseudomonas aeruginosa and Marinobacter hydrocarbonoclasticus," Int'l. Biodegrad. & Biodeter., vol. 93 (2014) 33-43.
E. G. Rawling et al. "Epitope Mapping of the Pseudomonas aeruginosa Major Outer Membrane Porin Protein Opr F", Infection and Immunity, vol. 63, 1, (1995), p. 38-42.
E. Sugawara et al. "Alternative folding pathways of the major porin OprF of Pseudomonas aeruginosa" FEBS Journal, 279 (2012), 910-918.
O. M. Pavlyuk et al. Peptide-Based Fluorescent Biosensing for Rapid Detection of Fuel Biocontaminants. Energy 7 Fuels, 2017, DOI:10.1021/acs.energyfuels.6b03350.
Dec. 11, 2018, Office Action for U.S. Pat. No. 10,295,537 B2.

* cited by examiner

*Primary Examiner* — Thomas S Heard
(74) *Attorney, Agent, or Firm* — AFMCLO/JAZ; James F. McBride

(57) ABSTRACT

A biorecognition element for rapid detection of fuel biocontamination. The biorecognition element is a biorecognition element selected from SEQ. ID No. 2 through SEQ. ID No. 24, SEQ. ID No. 22 through SEQ. ID No. 44, SEQ. ID No. 46 through SEQ. ID No. 57, SEQ. ID No. 59 through SEQ. ID No. 196 or SEQ. ID No. 198 through SEQ. ID No. 332.

13 Claims, 15 Drawing Sheets

Specification includes a Sequence Listing.

SEQUENCE LISTING

```
<160> NUMBER OF SEQ ID NOS: 332

<210> SEQ ID NO 1
<211> LENGTH: 28
<212> TYPE: PRT
<213> ORGANISM: Hormoconis resinae

<400> SEQUENCE: 1

Tyr Leu Pro Phe Asn Gly Gly Pro Arg Ile Cys Val Gly Gln Gln Phe
1               5                   10                  15

Ala Leu Ala Glu Ala Ser Tyr Ala Ile Val Arg Leu
            20                  25

<210> SEQ ID NO 2
<211> LENGTH: 7
<212> TYPE: PRT
<213> ORGANISM: Artificial Sequence
<220> FEATURE:
<223> OTHER INFORMATION: Artificial Sequence Obtained Through Biopanning
```

```
<400> SEQUENCE: 2

Trp Ser Leu Gly Tyr Thr Gly
1               5

<210> SEQ ID NO 3
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 3

Ala Tyr Ile His Pro Ile Met
1               5

<210> SEQ ID NO 4
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 4

Phe His His Ser Asn Tyr Gly
1               5

<210> SEQ ID NO 5
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 5

Gly Ser Phe Gly Tyr Ala Trp
1               5

<210> SEQ ID NO 6
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 6

Gly Ser Met Gly Ser Ile Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 7

Gly Ser Gln Gly Asp Asn Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 8
```

His Asn Phe Arg Thr Leu Val
1               5

<210> SEQ ID NO 9
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 9

His Asn Asn Pro Pro Ser Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 10

His Pro Ser Thr Trp His Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 11

His Ser Gly Gly Tyr Met Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 12

Leu Phe Leu Pro Ser Val Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 13

Asn Pro Phe Val Ala Ser Ser
1               5

<210> SEQ ID NO 14
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 14

Arg Ser Leu Gly Tyr His Gly
1               5

<210> SEQ ID NO 15
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 15

Ser Ile Val Glu Asp Leu Val
1               5

<210> SEQ ID NO 16
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 16

Ser Val Leu Tyr Phe Asp Val
1               5

<210> SEQ ID NO 17
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 17

Thr Cys Met Ser Glu Ala Cys
1               5

<210> SEQ ID NO 18
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 18

Thr Pro Thr Lys Thr Pro Trp
1               5

<210> SEQ ID NO 19
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 19

Val Ala Ser Pro Leu Phe Pro
1               5

<210> SEQ ID NO 20
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 20

Val Leu Ser Ala Val Pro Tyr

```
1               5

<210> SEQ ID NO 21
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 21

Val Trp Ala Gly Gly Tyr Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 22

Trp Gln Thr Glu Arg Ile Gly
1               5

<210> SEQ ID NO 23
<211> LENGTH: 6
<212> TYPE: PRT
<213> ORGANISM: Artificial Sequence
<220> FEATURE:
<223> OTHER INFORMATION: Artificial Sequence Obtained Through Biopanning

<400> SEQUENCE: 23

Trp Ser Ser Ser His Met
1               5

<210> SEQ ID NO 24
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 24

Tyr Ser Ser Leu Gly Asn Ser
1               5

<210> SEQ ID NO 25
<211> LENGTH: 16
<212> TYPE: PRT
<213> ORGANISM: Hormoconis resinae

<400> SEQUENCE: 25

Ile Pro Leu Cys Gln Gln Leu Gly Lys Ile Leu Leu Ser Leu Gly Gly
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 26

Met Pro Pro His Gly Asp Arg
1               5
```

```
<210> SEQ ID NO 27
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 27

Ala Ile Thr Ser Arg Asn Ala
1               5

<210> SEQ ID NO 28
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 28

Ala Met Thr His Met Pro Asn
1               5

<210> SEQ ID NO 29
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 29

Asp Thr Met Met Arg Leu Asn
1               5

<210> SEQ ID NO 30
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 30

Glu Thr Phe Leu Ile Thr Pro
1               5

<210> SEQ ID NO 31
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 31

Phe Ala Gly Thr Lys Asp Pro
1               5

<210> SEQ ID NO 32
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 32

Phe Ser His Lys Tyr Val Ile
1               5

<210> SEQ ID NO 33
```

```
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 33

Gly Asp Leu Tyr Pro Thr Thr
1               5

<210> SEQ ID NO 34
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 34

Gly Thr Phe Leu Phe Ser Pro
1               5

<210> SEQ ID NO 35
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 35

His Leu Thr Ser Glu Arg Leu
1               5

<210> SEQ ID NO 36
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 36

Met Gly Ile Arg Ala Gln Ala
1               5

<210> SEQ ID NO 37
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 37

Met Thr Thr His Met Asp Tyr
1               5

<210> SEQ ID NO 38
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 38

Asn Ile His His Leu Arg Phe
1               5

<210> SEQ ID NO 39
<211> LENGTH: 7
```

```
<212> TYPE: PRT
<213> ORGANISM: Artificial Sequence
<220> FEATURE:
<223> OTHER INFORMATION: Artificial Sequence Obtained Through Biopanning

<400> SEQUENCE: 39

Asn Ser Leu Ser Pro Ala Gly
1               5

<210> SEQ ID NO 40
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 40

Gln Asp Ala Gly Leu Tyr Trp
1               5

<210> SEQ ID NO 41
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 41

Gln Pro His Ile Ser Pro His
1               5

<210> SEQ ID NO 42
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 42

Ser Gln Ala Arg Pro Thr Ile
1               5

<210> SEQ ID NO 43
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 43

Ser Trp Ser Asn Trp Trp Glu
1               5

<210> SEQ ID NO 44
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 44

Thr Trp Thr Leu Ala Arg Pro
1               5

<210> SEQ ID NO 45
<211> LENGTH: 19
<212> TYPE: PRT
```

<213> ORGANISM: Hormoconis resinae

<400> SEQUENCE: 45

Cys Pro Asn Thr Lys Leu Val Ala Ser Gly Tyr Ser Gln Gly Gly Gln
1               5                   10                  15

Leu Val His

<210> SEQ ID NO 46
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 46

Ala Gly Asn Thr Asn Asn Ala
1               5

<210> SEQ ID NO 47
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 47

Ala Ile Thr Ser Arg Asn Ala
1               5

<210> SEQ ID NO 48
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 48

Ala Pro Met Val Leu Leu Ser
1               5

<210> SEQ ID NO 49
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 49

Phe Ala Gly Thr Lys Asp Pro
1               5

<210> SEQ ID NO 50
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 50

Phe Pro Phe Thr Tyr Leu Gln
1               5

<210> SEQ ID NO 51
<211> LENGTH: 7
<212> TYPE: PRT
<213> ORGANISM: Artificial Sequence

```
<220> FEATURE:
<223> OTHER INFORMATION: Artificial Sequence Obtained Through Biopanning

<400> SEQUENCE: 51

Gly Leu Leu Thr Gly His Thr
1               5

<210> SEQ ID NO 52
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 52

His Leu Thr Ser Glu Arg Leu
1               5

<210> SEQ ID NO 53
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 53

His Val Thr Asn Gly Leu Trp
1               5

<210> SEQ ID NO 54
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 54

Met Ile Asp Leu Gly Ala Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 55

Met Pro Thr Arg Val Ala Pro
1               5

<210> SEQ ID NO 56
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 56

Asn Ser Leu Ser Pro Ala Gly
1               5

<210> SEQ ID NO 57
<211> LENGTH: 7
<212> TYPE: PRT
<213> ORGANISM: Artificial Sequence
<220> FEATURE:
```

```
<223> OTHER INFORMATION: Artificial Sequence Obtained Through Biopanning

<400> SEQUENCE: 57

Thr Ser Phe Ala Asn Ser Met
1               5

<210> SEQ ID NO 58
<211> LENGTH: 25
<212> TYPE: PRT
<213> ORGANISM: Gordonia sihwensis strain 9

<400> SEQUENCE: 58

Ala Leu Ser Gly Lys Leu Asn Pro Gln Val Asn Leu Val Asp Thr Leu
1               5                   10                  15

Asn Gly Gly Glu Phe Thr Val Phe Ala
            20                  25

<210> SEQ ID NO 59
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 59

Thr Trp Thr Leu Ala Arg Pro
1               5

<210> SEQ ID NO 60
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 60

Arg Ser Leu Gly Tyr Thr Gly
1               5

<210> SEQ ID NO 61
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 61

Tyr Val Pro Glu Trp Val Ser
1               5

<210> SEQ ID NO 62
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 62

Gln Gly Gly Ile Ser Thr Thr
1               5

<210> SEQ ID NO 63
<211> LENGTH: 7
<212> TYPE: PRT
<213> ORGANISM: Artificial Sequence
<220> FEATURE:
```

```
<223> OTHER INFORMATION: Artificial Sequence Obtained Through Biopanning

<400> SEQUENCE: 63

Met Ile Thr Gly Thr Gln Pro
1               5

<210> SEQ ID NO 64
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 64

Ser Met Ser Leu Asp Asp Gly
1               5

<210> SEQ ID NO 65
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 65

Gly Ile Leu Val Pro Pro Thr
1               5

<210> SEQ ID NO 66
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 66

Phe Gly Pro Ile Gly Thr Trp
1               5

<210> SEQ ID NO 67
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 67

Tyr Thr Asp Arg Phe Tyr Met
1               5

<210> SEQ ID NO 68
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 68

Met Val Leu Pro Pro Pro Ala
1               5

<210> SEQ ID NO 69
<211> LENGTH: 7
<212> TYPE: PRT
<213> ORGANISM: Artificial Sequence
<220> FEATURE:
<223> OTHER INFORMATION: Artificial Sequence Obtained Through Biopanning
```

<400> SEQUENCE: 69

Trp His Arg Pro Phe Leu Leu
1               5

<210> SEQ ID NO 70
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 70

Ser Asp Asp Ile Arg Arg Asn
1               5

<210> SEQ ID NO 71
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 71

Phe Gln Thr Gly Asp Glu Arg
1               5

<210> SEQ ID NO 72
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 72

Trp Ser Leu Gly Tyr Thr Gly
1               5

<210> SEQ ID NO 73
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 73

Met Leu Gln Ser Ser Leu Ser
1               5

<210> SEQ ID NO 74
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 74

Tyr Thr Pro Leu Tyr Ala Arg
1               5

<210> SEQ ID NO 75
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 75

Phe Ser Phe Gly Thr Arg Pro
1               5

<210> SEQ ID NO 76
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 76

Lys Ser Ser Trp Glu Phe Ala
1               5

<210> SEQ ID NO 77
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 77

Val Thr Leu Val Asn Gly Ile
1               5

<210> SEQ ID NO 78
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 78

Ile Ser Phe Thr Pro Lys Thr
1               5

<210> SEQ ID NO 79
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 79

Leu Gln Ala Met Pro Asn Arg
1               5

<210> SEQ ID NO 80
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 80

Phe Pro Gly Ser Ser Pro Lys
1               5

<210> SEQ ID NO 81
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 81

```
Thr Lys Thr Pro His Ile His
1               5
```

<210> SEQ ID NO 82
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 82

```
Val Ser His Val Ile Asn Asp
1               5
```

<210> SEQ ID NO 83
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 83

```
His Val Thr Asn Gly Leu Trp
1               5
```

<210> SEQ ID NO 84
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 84

```
His Ile Leu Asn Trp Pro Thr
1               5
```

<210> SEQ ID NO 85
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 85

```
Asn Asn Trp Phe Ser Phe Asp
1               5
```

<210> SEQ ID NO 86
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 86

```
Tyr Trp Thr Ser Gly Gln Leu
1               5
```

<210> SEQ ID NO 87
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 87

```
Gly Arg Asn Leu Ile Glu Met
1               5

<210> SEQ ID NO 88
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 88

Gly Ser Phe Gly Tyr Thr Arg
1               5

<210> SEQ ID NO 89
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 89

Cys Asp Phe Arg Ser Ile Lys
1               5

<210> SEQ ID NO 90
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 90

Trp His Trp Gln Thr Arg Gly
1               5

<210> SEQ ID NO 91
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 91

Ser Thr Ala Leu Pro Phe Arg
1               5

<210> SEQ ID NO 92
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 92

Tyr Ile Pro Gly Thr Val Pro
1               5

<210> SEQ ID NO 93
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 93

Ser Met Ser Ile Ser Ser Arg
```

```
1               5

<210> SEQ ID NO 94
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 94

Trp Ser Trp His His Ser Gly
1               5

<210> SEQ ID NO 95
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 95

Glu His Val Glu Pro Ser Arg
1               5

<210> SEQ ID NO 96
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 96

Asn Gln Phe Ser Leu Ser Gln
1               5

<210> SEQ ID NO 97
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 97

Tyr Lys Phe Gly Gln Gln Gly
1               5

<210> SEQ ID NO 98
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 98

His Tyr Gly Thr Tyr Asn Val
1               5

<210> SEQ ID NO 99
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 99

Thr Gly Tyr Pro Leu Glu Ser
1               5
```

```
<210> SEQ ID NO 100
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 100

Phe Thr Thr Phe Thr Ser Asn
1               5

<210> SEQ ID NO 101
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 101

Ser Trp Pro Ser Arg Ile Pro
1               5

<210> SEQ ID NO 102
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 102

Tyr Pro Asp Tyr Leu Ala Arg
1               5

<210> SEQ ID NO 103
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 103

Asn His Trp Val Gln Tyr Phe
1               5

<210> SEQ ID NO 104
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 104

Lys Ile Val His Arg Leu Tyr
1               5

<210> SEQ ID NO 105
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 105

Ile Asn Gln Thr Gln Leu Thr
1               5
```

```
<210> SEQ ID NO 106
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 106

Tyr Thr Gln Gly His Leu Leu
1               5

<210> SEQ ID NO 107
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 107

Asp Thr Lys Tyr Met Thr Ser
1               5

<210> SEQ ID NO 108
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 108

Met Leu Leu Gly Glu Thr Gly
1               5

<210> SEQ ID NO 109
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 109

Asn Met Leu His Ala Leu Tyr
1               5

<210> SEQ ID NO 110
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 110

Leu Pro Gln Phe Gln Asn Cys
1               5

<210> SEQ ID NO 111
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 111

Leu Pro Gln Val Gln Thr Cys
1               5
```

```
<210> SEQ ID NO 112
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 112

Ser Glu Asn Pro His Phe Lys
1               5

<210> SEQ ID NO 113
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 113

Asn Tyr Tyr Ser Ala Lys Thr
1               5

<210> SEQ ID NO 114
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 114

Asn Asn Asp Met Pro Ala Pro
1               5

<210> SEQ ID NO 115
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 115

His Phe Leu Asn Ala Gln His
1               5

<210> SEQ ID NO 116
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 116

Ser Trp Trp Arg Ser Glu Leu
1               5

<210> SEQ ID NO 117
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 117

Leu Gln Tyr Ser Thr Arg Leu
1               5

<210> SEQ ID NO 118
```

```
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 118

Ser Ser Tyr Ile Asp Tyr Arg
1               5

<210> SEQ ID NO 119
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 119

Asn Asp Ser Lys Thr Pro Ser
1               5

<210> SEQ ID NO 120
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 120

His Gly Asp His Val Ser His
1               5

<210> SEQ ID NO 121
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 121

Tyr Ser Ser Leu Trp Leu Gln
1               5

<210> SEQ ID NO 122
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 122

Tyr His Asn Gln Lys Ser Trp
1               5

<210> SEQ ID NO 123
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 123

Gly Lys Leu Pro Pro Arg Tyr
1               5

<210> SEQ ID NO 124
<211> LENGTH: 7
```

```
<212> TYPE: PRT
<213> ORGANISM: Artificial Sequence
<220> FEATURE:
<223> OTHER INFORMATION: Artificial Sequence Obtained Through Biopanning

<400> SEQUENCE: 124

Phe Pro Leu Arg Ala Pro Ser
1               5

<210> SEQ ID NO 125
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 125

Ile Gly Ala Leu Asp Ala Arg
1               5

<210> SEQ ID NO 126
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 126

Lys Pro Met Leu Phe Phe Gly
1               5

<210> SEQ ID NO 127
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 127

Ser Thr Met Tyr Thr Val Tyr
1               5

<210> SEQ ID NO 128
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 128

Leu His Ala Ser Ile Pro Pro
1               5

<210> SEQ ID NO 129
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 129

His Leu Ser Leu Ala Met Arg
1               5

<210> SEQ ID NO 130
<211> LENGTH: 7
<212> TYPE: PRT
```

```
<213> ORGANISM: Artificial Sequence
<220> FEATURE:
<223> OTHER INFORMATION: Artificial Sequence Obtained Through Biopanning

<400> SEQUENCE: 130

Leu Ser Trp Pro Lys Phe Leu
1               5

<210> SEQ ID NO 131
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 131

Gln Gly Asp Gln Glu Ser Arg
1               5

<210> SEQ ID NO 132
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 132

Ala Leu Ser Ser Ile Leu Thr
1               5

<210> SEQ ID NO 133
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 133

Ser Val Ala Leu Gly Ala Tyr
1               5

<210> SEQ ID NO 134
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 134

Arg Ser Leu Gly Tyr Pro Gly
1               5

<210> SEQ ID NO 135
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 135

Phe His Gly Ile Pro Ser Val
1               5

<210> SEQ ID NO 136
<211> LENGTH: 7
<212> TYPE: PRT
<213> ORGANISM: Artificial Sequence
```

```
<220> FEATURE:
<223> OTHER INFORMATION: Artificial Sequence Obtained Through Biopanning

<400> SEQUENCE: 136

Trp Ser Leu Arg Tyr Thr Arg
1               5

<210> SEQ ID NO 137
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 137

Trp Ser Leu Gly Tyr Thr Trp
1               5

<210> SEQ ID NO 138
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 138

Trp Ser His Gly Tyr Thr Gly
1               5

<210> SEQ ID NO 139
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 139

Leu Glu Ser Phe Tyr Thr Gly
1               5

<210> SEQ ID NO 140
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 140

Trp Thr Asn Pro Tyr Leu Ala Leu Asp His Pro Met
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 141

Trp Lys Asn Pro Tyr Leu Ala Leu Asp His Pro Met
1               5                   10

<210> SEQ ID NO 142
<211> LENGTH: 12
<212> TYPE: PRT
<213> ORGANISM: Artificial Sequence
<220> FEATURE:
```

<223> OTHER INFORMATION: Artificial Sequence Obtained Through Biopanning

<400> SEQUENCE: 142

Trp Arg Asn Pro Tyr Leu Ala Leu Asp His Pro Met
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 143

Lys His His His Val His His
1               5

<210> SEQ ID NO 144
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 144

His His His His Arg Pro His
1               5

<210> SEQ ID NO 145
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 145

His His His His His Thr Arg
1               5

<210> SEQ ID NO 146
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 146

His Arg His His Trp His His
1               5

<210> SEQ ID NO 147
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 147

Arg Ala Met Asp Arg Met Pro
1               5

<210> SEQ ID NO 148
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 148

Trp Pro Asn His His His Pro Arg Ala His Thr
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 149

His His Thr Ser His Lys Thr His Pro His Leu His
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 150

Tyr Gly His His His His Ala His His Ile Arg Ser
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 151

His His Ser Pro His Lys His Pro Ile His Gly Lys
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 152

His His Ser His His Val His Gln Gly Met Arg Pro
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 153

His Ser His His Leu Pro Tyr Met His Lys Thr Arg
1               5                   10

<210> SEQ ID NO 154
<211> LENGTH: 12
<212> TYPE: PRT
<213> ORGANISM: Artificial Sequence
<220> FEATURE:
<223> OTHER INFORMATION: Artificial Sequence Obtained Through Biopanning

```
<400> SEQUENCE: 154

Val Asp Leu Asn Pro Ser Gly Arg Phe Gln Ile Ser
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 155

His His His His Ser Ile Arg Gly His Ser Gly Ser
1               5                   10

<210> SEQ ID NO 156
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 156

His Ser His Gly His Leu Arg His His Met Val Asn
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 157

Ser Leu His Asp Gln His Ala Ser Leu Gln Arg Asp
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 158

His Lys Met Pro His His His Gln Arg Gly Ile
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 159

Glu Ser Gly Arg Gly Pro Asp Glu Gly Lys Ser Pro
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 160
```

```
Ala Leu His Gly His His Arg Trp His Lys Thr His
1               5                   10
```

<210> SEQ ID NO 161
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 161

```
His Ser His His Leu His Tyr Met His Lys Thr Arg
1               5                   10
```

<210> SEQ ID NO 162
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 162

```
His Ile Gly His His His His Ser Lys Met Arg Thr
1               5                   10
```

<210> SEQ ID NO 163
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 163

```
Ser Val Arg His His Val His His Ser His Trp Ser
1               5                   10
```

<210> SEQ ID NO 164
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 164

```
His His His Gly Glu Arg Leu His His His Ser Tyr
1               5                   10
```

<210> SEQ ID NO 165
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 165

```
Gly His His Val His His Lys His Pro Val Asn His
1               5                   10
```

<210> SEQ ID NO 166
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 166

```
Ser Gln His His His Ile Lys His Tyr Met Thr
1               5                   10
```

<210> SEQ ID NO 167
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 167

```
Leu Asp Arg Pro Ser Ser Leu Ala His Leu Ala Ser
1               5                   10
```

<210> SEQ ID NO 168
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 168

```
Ser Tyr Ser His His Tyr His Lys His His Gly His
1               5                   10
```

<210> SEQ ID NO 169
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 169

```
Ala His Phe Cys Thr Ala Ser His Cys His Ala Arg
1               5                   10
```

<210> SEQ ID NO 170
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 170

```
Asn Pro His His His Arg Asn Gln His His Ser Ile
1               5                   10
```

<210> SEQ ID NO 171
<211> LENGTH: 11
<212> TYPE: PRT
<213> ORGANISM: Artificial Sequence
<220> FEATURE:
<223> OTHER INFORMATION: Artificial Sequence Obtained Through Biopanning

<400> SEQUENCE: 171

```
Gly Glu Asp Asn Arg Val Asn Asp Pro Ala Arg
1               5                   10
```

<210> SEQ ID NO 172
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 172

```
Ala Arg His His His Ser His Val His Trp Leu Arg
```

```
1               5                   10
```

<210> SEQ ID NO 173
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 173

```
His His His His Arg Leu Asn Thr Ser Ser Lys His
1               5                   10
```

<210> SEQ ID NO 174
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 174

```
Gly Tyr Lys His His His Arg Thr His Thr Thr Ala
1               5                   10
```

<210> SEQ ID NO 175
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 175

```
Gly Asn Asn Pro Leu His Val His His Asp Lys Arg
1               5                   10
```

<210> SEQ ID NO 176
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 176

```
Leu Ala Pro Thr Tyr Ile Met Trp Gly Thr Ser Ser
1               5                   10
```

<210> SEQ ID NO 177
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 177

```
Asp Tyr His Asp Pro Ser Leu Pro Thr Leu Arg Lys
1               5                   10
```

<210> SEQ ID NO 178
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 178

```
Ala His Asp Pro Phe Pro Met Arg Leu Leu Arg Ala
1               5                   10
```

```
<210> SEQ ID NO 179
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 179

Asp Met Lys Ala Arg Val Ala
1               5

<210> SEQ ID NO 180
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 180

Ser Ile Ala His Asn Thr Met
1               5

<210> SEQ ID NO 181
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 181

Leu Val Thr Val Pro Arg Ser
1               5

<210> SEQ ID NO 182
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 182

Gly Asp Met Leu Thr Leu Arg
1               5

<210> SEQ ID NO 183
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 183

His Ser Ser Thr Val Thr Ile
1               5

<210> SEQ ID NO 184
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 184

Phe Ala Leu Thr Pro Pro Pro
1               5
```

<210> SEQ ID NO 185
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 185

Gln Asn Asn Ile His Thr Pro
1               5

<210> SEQ ID NO 186
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 186

Gln Ala His Trp Leu Arg Glu
1               5

<210> SEQ ID NO 187
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 187

Thr Met Ile Asp Ala Asn Arg
1               5

<210> SEQ ID NO 188
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 188

Gly Ser Phe Ile Ile His Thr
1               5

<210> SEQ ID NO 189
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 189

Tyr Gly Thr Ser Leu Ser Arg
1               5

<210> SEQ ID NO 190
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 190

His Gly Lys Ile Leu Leu Thr
1               5

```
<210> SEQ ID NO 191
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 191

Gly Pro Tyr Ser Val Leu Ala
1               5

<210> SEQ ID NO 192
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 192

Tyr Ser Leu Ser Leu Pro Glu
1               5

<210> SEQ ID NO 193
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 193

Gly Cys Lys Arg Tyr Thr Gly
1               5

<210> SEQ ID NO 194
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 194

Trp Ser Leu Gly Tyr Thr Gly
1               5

<210> SEQ ID NO 195
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 195

Trp Val Met Asn His Pro Gln
1               5

<210> SEQ ID NO 196
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 196

Arg Leu Leu Gly His Thr Arg
1               5

<210> SEQ ID NO 197
```

```
<211> LENGTH: 24
<212> TYPE: PRT
<213> ORGANISM: Nocardioides luteus

<400> SEQUENCE: 197

Asn Val Asn Gly Asp Thr Met Val Ala Leu Leu Val Ala His Gly Ala
1               5                   10                  15

Gly Glu Ile Asp Arg Asp Val Tyr
            20

<210> SEQ ID NO 198
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 198

Ser Gly Phe Pro Val Lys Asp
1               5

<210> SEQ ID NO 199
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 199

Asp Pro Leu His Met Lys Lys
1               5

<210> SEQ ID NO 200
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 200

Ser Asp Phe Phe Thr Thr Ser
1               5

<210> SEQ ID NO 201
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 201

Phe Asp Ile Ala Ser Pro Ser
1               5

<210> SEQ ID NO 202
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 202

Thr Ser Gln Val Asn His Asp
1               5

<210> SEQ ID NO 203
```

```
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 203

Asn Val Leu Ser Pro Pro Phe
1               5

<210> SEQ ID NO 204
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 204

Tyr Thr Leu Pro Lys Ala Arg
1               5

<210> SEQ ID NO 205
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 205

Leu Leu Asn Pro Trp Thr His
1               5

<210> SEQ ID NO 206
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 206

Glu His Ala Ile Gln Tyr Pro
1               5

<210> SEQ ID NO 207
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 207

Ser His Val Leu Ser Val Ala
1               5

<210> SEQ ID NO 208
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 208

His Asp Ser Val His Phe Asp
1               5

<210> SEQ ID NO 209
<211> LENGTH: 7
```

```
<212> TYPE: PRT
<213> ORGANISM: Artificial Sequence
<220> FEATURE:
<223> OTHER INFORMATION: Artificial Sequence Obtained Through Biopanning

<400> SEQUENCE: 209

Val Pro Trp Pro Met Ser Ile
1               5

<210> SEQ ID NO 210
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 210

Val Pro Arg Thr Ala Phe Trp
1               5

<210> SEQ ID NO 211
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 211

Met Thr Asp Phe Val Phe Ser
1               5

<210> SEQ ID NO 212
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 212

Ala Lys Leu Val Ser Arg Val
1               5

<210> SEQ ID NO 213
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 213

Ile Pro Trp Tyr Trp Tyr Leu
1               5

<210> SEQ ID NO 214
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 214

Val Ile His Arg Pro Met Thr
1               5

<210> SEQ ID NO 215
<211> LENGTH: 7
<212> TYPE: PRT
```

<213> ORGANISM: Artificial Sequence
<220> FEATURE:
<223> OTHER INFORMATION: Artificial Sequence Obtained Through Biopanning

<400> SEQUENCE: 215

Tyr Leu Thr Asp Ser Trp Asp
1               5

<210> SEQ ID NO 216
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 216

Thr Pro Arg Ser Ser His Pro
1               5

<210> SEQ ID NO 217
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 217

Gly Cys Ala Pro Tyr Lys Arg
1               5

<210> SEQ ID NO 218
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 218

Lys Thr Ser Leu Glu Ser Ile
1               5

<210> SEQ ID NO 219
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 219

Trp Ser Leu Gly Tyr Thr Gly
1               5

<210> SEQ ID NO 220
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 220

Lys Leu Pro Gln Ile Ala Ser
1               5

<210> SEQ ID NO 221
<211> LENGTH: 7
<212> TYPE: PRT
<213> ORGANISM: Artificial Sequence

```
<220> FEATURE:
<223> OTHER INFORMATION: Artificial Sequence Obtained Through Biopanning

<400> SEQUENCE: 221

Ser His Asn Thr Trp Met Pro
1               5

<210> SEQ ID NO 222
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 222

Asn Leu Ala Pro Phe Thr Phe
1               5

<210> SEQ ID NO 223
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 223

Tyr Gly Asp Met Pro Arg Phe
1               5

<210> SEQ ID NO 224
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 224

Gly Met His Gly Lys Cys Tyr Gly Arg Glu Leu Cys
1               5                   10

<210> SEQ ID NO 225
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 225

Ser Val Asp Gly Trp Leu Glu Pro Pro Thr Ser Thr
1               5                   10

<210> SEQ ID NO 226
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 226

Gln Val Asn Gly Leu Gly Glu Arg Ser Gln Gln Met
1               5                   10

<210> SEQ ID NO 227
<211> LENGTH: 12
<212> TYPE: PRT
<213> ORGANISM: Artificial Sequence
<220> FEATURE:
```

```
<223> OTHER INFORMATION: Artificial Sequence Obtained Through Biopanning

<400> SEQUENCE: 227

Arg Asp Tyr His Pro Arg Asp His Thr Ala Thr Trp
1               5                   10

<210> SEQ ID NO 228
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 228

Thr Tyr Ala Met Leu Ala Arg Val Asp Gly Leu Ser
1               5                   10

<210> SEQ ID NO 229
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 229

Gly Asn Asn Pro Leu His Val His His Asp Lys Arg
1               5                   10

<210> SEQ ID NO 230
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 230

Asp Tyr His Asp Pro Ser Leu Pro Thr Leu Arg Lys
1               5                   10

<210> SEQ ID NO 231
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 231

Ser Gly Leu Asn Tyr Ser Trp Pro Glu Val Lys Asn
1               5                   10

<210> SEQ ID NO 232
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 232

Val Pro Pro Glu Gly Pro Met Glu Arg Tyr Ile Gly
1               5                   10

<210> SEQ ID NO 233
<211> LENGTH: 12
<212> TYPE: PRT
<213> ORGANISM: Artificial Sequence
<220> FEATURE:
<223> OTHER INFORMATION: Artificial Sequence Obtained Through Biopanning
```

<400> SEQUENCE: 233

His Ser His His Arg His His His Leu Asn Asn Arg
1               5                   10

<210> SEQ ID NO 234
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 234

Ser Leu Leu Ala Glu Arg Gln Phe Asn Ser Lys Pro
1               5                   10

<210> SEQ ID NO 235
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 235

Tyr Gly His His His Ala His His Ile Arg Ser
1               5                   10

<210> SEQ ID NO 236
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 236

Tyr Pro Val Glu Thr His Leu Ser Ala Arg Val Ile
1               5                   10

<210> SEQ ID NO 237
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 237

Arg Asp Tyr His Pro Arg Asp His Thr Ala Thr Trp
1               5                   10

<210> SEQ ID NO 238
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 238

Asp Tyr His Asp Pro Ser Leu Leu Pro Met Arg Lys
1               5                   10

<210> SEQ ID NO 239
<211> LENGTH: 12
<212> TYPE: PRT
<213> ORGANISM: Artificial Sequence
<220> FEATURE:
<223> OTHER INFORMATION: Artificial Sequence Obtained Through Biopanning

```
<400> SEQUENCE: 239

Arg Asp His His Pro Arg Asp His Thr Val Arg Arg
1               5                   10

<210> SEQ ID NO 240
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 240

Lys Pro His Trp Lys Asn Gln Asp Gly Leu Met Ile
1               5                   10

<210> SEQ ID NO 241
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 241

Trp Glu Asn Val Pro Ile Thr Gln Gln Arg Pro Arg
1               5                   10

<210> SEQ ID NO 242
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 242

Lys Val Tyr His Glu Gly Leu Ser Met Lys Lys His
1               5                   10

<210> SEQ ID NO 243
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 243

Asp Asn His Asp Pro Ser Leu Pro Pro Asp Lys Lys
1               5                   10

<210> SEQ ID NO 244
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 244

Asp Tyr His Asp Pro Ser Leu Pro Pro Gln Lys Lys
1               5                   10

<210> SEQ ID NO 245
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 245
```

```
Lys Leu Trp Ser Ile Pro Thr Asn Phe Leu Leu Pro
1               5                   10
```

<210> SEQ ID NO 246
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 246

```
Ser Leu Glu Tyr Pro Gly Glu Arg Thr Gln Arg Lys
1               5                   10
```

<210> SEQ ID NO 247
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 247

```
Lys Pro Gly Phe Asp Val Cys Ala Trp Trp Arg Cys
1               5                   10
```

<210> SEQ ID NO 248
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 248

```
Leu Ser Ser Gly Ser Lys Phe Ala Tyr Ala Ala Lys
1               5                   10
```

<210> SEQ ID NO 249
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 249

```
Asn Ile His Arg Pro Ile Leu
1               5
```

<210> SEQ ID NO 250
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 250

```
Pro Ser Leu Ile Thr Pro Val
1               5
```

<210> SEQ ID NO 251
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 251

```
Leu Thr Ser Leu Asp Thr Tyr
1               5

<210> SEQ ID NO 252
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 252

Glu Val Ile Gly Thr Pro Lys
1               5

<210> SEQ ID NO 253
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 253

Thr Ile Trp Asp Ser Phe Thr
1               5

<210> SEQ ID NO 254
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 254

Arg Phe Pro Thr Ser Phe Asp
1               5

<210> SEQ ID NO 255
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 255

Thr Tyr Pro Thr Leu Thr Ile
1               5

<210> SEQ ID NO 256
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 256

Ser Val Leu Arg Met Leu Asn
1               5

<210> SEQ ID NO 257
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 257

His Ser Leu Ile Met Pro Ala
```

-continued

```
1               5

<210> SEQ ID NO 258
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 258

Tyr Pro Leu Gly Leu Thr Arg
1               5

<210> SEQ ID NO 259
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 259

Met Leu Ser Leu Pro Gln Gln
1               5

<210> SEQ ID NO 260
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 260

Asn Leu Tyr Pro Pro Leu Ser
1               5

<210> SEQ ID NO 261
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 261

His Gln Val Ala Phe Lys Ile
1               5

<210> SEQ ID NO 262
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 262

Trp His Tyr Pro Leu Ser Val
1               5

<210> SEQ ID NO 263
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 263

Gln Ser Ile Pro Ser Tyr Trp
1               5
```

```
<210> SEQ ID NO 264
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 264

Tyr Pro Pro Leu Ala Gly His
1               5

<210> SEQ ID NO 265
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 265

Trp Pro Thr Arg Leu Ser Glu
1               5

<210> SEQ ID NO 266
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 266

Arg Ser His Gly Tyr Ser Gly
1               5

<210> SEQ ID NO 267
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 267

Arg Ser Gln Gly Tyr His Gly
1               5

<210> SEQ ID NO 268
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 268

Asn Asn Ile Val Ala Arg Trp
1               5

<210> SEQ ID NO 269
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 269

Gly Asn Leu Ser Ser Ala Ala
1               5
```

```
<210> SEQ ID NO 270
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 270

Thr His Ser Thr Pro Ser Leu
1               5

<210> SEQ ID NO 271
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 271

Val Val Pro Thr Arg Val Tyr
1               5

<210> SEQ ID NO 272
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 272

His Met Pro Cys Leu Leu Leu
1               5

<210> SEQ ID NO 273
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 273

Gly Thr Ile Tyr Trp Asn Ser
1               5

<210> SEQ ID NO 274
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 274

Ala Ser Trp Ala Pro Met Pro
1               5

<210> SEQ ID NO 275
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 275

Asp Leu Gly Pro Arg Pro Leu
1               5
```

```
<210> SEQ ID NO 276
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 276

Thr Leu Thr Ser Gly Val Leu
1               5

<210> SEQ ID NO 277
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 277

Leu Glu Leu Asp Pro Ser Gln Leu Tyr Ala His His
1               5                   10

<210> SEQ ID NO 278
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 278

Gly Val His Ser Val Phe Ala Pro Leu Thr Pro Asn
1               5                   10

<210> SEQ ID NO 279
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 279

Ser Ser Ser Gly Val Met His Gly Pro Pro Val Leu
1               5                   10

<210> SEQ ID NO 280
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 280

Thr Ala Lys Tyr Leu Pro Met Arg Pro Gly Pro Leu
1               5                   10

<210> SEQ ID NO 281
<211> LENGTH: 11
<212> TYPE: PRT
<213> ORGANISM: Artificial Sequence
<220> FEATURE:
<223> OTHER INFORMATION: Artificial Sequence Obtained Through Biopanning

<400> SEQUENCE: 281

Ser Glu Val Leu Thr Phe Ala Trp Trp Arg Cys
1               5                   10

<210> SEQ ID NO 282
```

```
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 282

His His Leu Arg Ile Pro Tyr Ala Leu Asp Gln Thr
1               5                   10

<210> SEQ ID NO 283
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 283

Lys Pro Gly Phe Asp Val Cys Ala Trp Arg Arg Cys
1               5                   10

<210> SEQ ID NO 284
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 284

Lys Leu Gly Phe Asp Val Cys Ala Trp Arg Arg Trp
1               5                   10

<210> SEQ ID NO 285
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 285

Thr Ser Trp Arg His Val Glu
1               5

<210> SEQ ID NO 286
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 286

Ile Val Asn Gln Gly Leu Pro
1               5

<210> SEQ ID NO 287
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 287

Gln Ser Pro Thr His Pro Ser
1               5

<210> SEQ ID NO 288
<211> LENGTH: 7
```

```
<212> TYPE: PRT
<213> ORGANISM: Artificial Sequence
<220> FEATURE:
<223> OTHER INFORMATION: Artificial Sequence Obtained Through Biopanning

<400> SEQUENCE: 288

Arg Ser Leu Gly Tyr Thr Gly
1               5

<210> SEQ ID NO 289
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 289

Leu Lys Thr Gly Asp Leu Arg
1               5

<210> SEQ ID NO 290
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 290

Ser Asp Arg Ile Leu Tyr Leu
1               5

<210> SEQ ID NO 291
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 291

Lys Asp Leu Pro Val Thr Pro
1               5

<210> SEQ ID NO 292
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 292

Ser Leu Leu Ser Phe Asp Arg
1               5

<210> SEQ ID NO 293
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 293

Gln Ser Asn Ala Val Arg Ile
1               5

<210> SEQ ID NO 294
<211> LENGTH: 7
<212> TYPE: PRT
```

```
<213> ORGANISM: Artificial Sequence
<220> FEATURE:
<223> OTHER INFORMATION: Artificial Sequence Obtained Through Biopanning

<400> SEQUENCE: 294

His Ser Arg Leu Pro Thr Pro
1               5

<210> SEQ ID NO 295
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 295

Ser Val Gln Phe Ile His Asp
1               5

<210> SEQ ID NO 296
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 296

Thr Gln Phe Leu Glu Met Val
1               5

<210> SEQ ID NO 297
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 297

His Val Phe Ala Leu Val His
1               5

<210> SEQ ID NO 298
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 298

Gly Asn Leu Ile Asn Ile Asp
1               5

<210> SEQ ID NO 299
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 299

Glu Phe Val Met Tyr Ser Arg
1               5

<210> SEQ ID NO 300
<211> LENGTH: 7
<212> TYPE: PRT
<213> ORGANISM: Artificial Sequence
```

```
<220> FEATURE:
<223> OTHER INFORMATION: Artificial Sequence Obtained Through Biopanning

<400> SEQUENCE: 300

Lys Asp Leu Pro Val Thr Pro
1               5

<210> SEQ ID NO 301
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 301

Gly Ile Ile Gly Asp Thr Pro
1               5

<210> SEQ ID NO 302
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 302

Thr Cys Ala Asn Cys Trp Pro
1               5

<210> SEQ ID NO 303
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 303

Gly Met Lys Pro His Ala Tyr
1               5

<210> SEQ ID NO 304
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 304

Ser Thr Val His Lys Gln Ile
1               5

<210> SEQ ID NO 305
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 305

Leu Met Thr Asp Asp Pro Arg
1               5

<210> SEQ ID NO 306
<211> LENGTH: 7
<212> TYPE: PRT
<213> ORGANISM: Artificial Sequence
<220> FEATURE:
```

<223> OTHER INFORMATION: Artificial Sequence Obtained Through Biopanning

<400> SEQUENCE: 306

Asn Gly Thr Thr Ile Tyr Ser
1               5

<210> SEQ ID NO 307
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 307

Tyr Ser Phe Gly Asp Trp Arg
1               5

<210> SEQ ID NO 308
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 308

Trp Ser Leu Gly Tyr Thr Gly
1               5

<210> SEQ ID NO 309
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 309

Val Gly Ser Pro Leu Thr Pro
1               5

<210> SEQ ID NO 310
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 310

Trp Thr Gln Tyr Tyr Pro Trp
1               5

<210> SEQ ID NO 311
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 311

Met Asn Tyr Tyr Asp Ala Tyr
1               5

<210> SEQ ID NO 312
<211> LENGTH: 7
<212> TYPE: PRT
<213> ORGANISM: Artificial Sequence
<220> FEATURE:
<223> OTHER INFORMATION: Artificial Sequence Obtained Through Biopanning

```
<400> SEQUENCE: 312

Val Pro Tyr Pro Thr Ile Arg
1               5

<210> SEQ ID NO 313
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 313

Met Asp Leu Ser Val Gly Val
1               5

<210> SEQ ID NO 314
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 314

Glu Gly Phe Ser His Trp Ser
1               5

<210> SEQ ID NO 315
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 315

Ser Tyr Gln Thr Ser Thr Ser
1               5

<210> SEQ ID NO 316
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 316

His Lys Leu Asn Thr Pro Pro
1               5

<210> SEQ ID NO 317
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 317

His Arg His His His Ser His
1               5

<210> SEQ ID NO 318
<211> LENGTH: 7
<212> TYPE: PRT
<213> ORGANISM: Artificial Sequence
<220> FEATURE:
<223> OTHER INFORMATION: Artificial Sequence Obtained Through Biopanning
```

```
<400> SEQUENCE: 318

His His His His Arg Pro His
1               5

<210> SEQ ID NO 319
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 319

His Lys His Leu His His His
1               5

<210> SEQ ID NO 320
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 320

His Lys His Gly His His His
1               5

<210> SEQ ID NO 321
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 321

His His Lys His Val His Arg
1               5

<210> SEQ ID NO 322
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 322

His His His His His Thr Arg
1               5

<210> SEQ ID NO 323
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 323

Ser Thr Thr Gly Thr Gln Tyr
1               5

<210> SEQ ID NO 324
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 324
```

```
Asp Phe Ala Gln Trp Tyr Leu
1               5
```

<210> SEQ ID NO 325
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 325

```
Val His Val Gln Ala Thr Ser
1               5
```

<210> SEQ ID NO 326
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 326

```
Glu Ser Gly Arg Met Ala His
1               5
```

<210> SEQ ID NO 327
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 327

```
Asp Ile Thr Arg Phe Leu Leu
1               5
```

<210> SEQ ID NO 328
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 328

```
Trp Ser Ile Val Asn Ala Gly
1               5
```

<210> SEQ ID NO 329
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 329

```
Gly Ser Leu Gly Tyr Thr Arg
1               5
```

<210> SEQ ID NO 330
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 330

```
Thr Ser Asp Ser Glu Ala Arg
1               5

<210> SEQ ID NO 331
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 331

His Tyr His Cys Asn Pro Trp
1               5

<210> SEQ ID NO 332
<211> LENGTH: 7
<212> TYPE: PRT
<213> ORGANISM: Artificial Sequence
<220> FEATURE:
<223> OTHER INFORMATION: Artificial Sequence Obtained Through Biopanning

<400> SEQUENCE: 332

Trp Ser Ile Val Asn Ala Gly
1               5
```

BIORECOGNITION ELEMENTS FOR DETECTION OF FUNGI AND BACTERIA IN FUEL SYSTEMS

INCORPORATION-BY-REFERENCE OF ASCII SEQUENCE TEXT FILE AND CROSS-REFERENCE TO RELATED APPLICATION

The ASCII Sequence Text File named AFD-2013_ST25 that was created on May 20, 2021, and has a size of 71,952 bytes is hereby incorporated in the present application by reference in its entry. In addition, the present application claims priority to U.S. Provisional Application Ser. No. 63/186,844 filed May 11, 2021, and U.S. Provisional Application Ser. No. 63/026,853 filed May 19, 2020, the contents of both such provisional applications hereby being incorporated by reference in their entry.

RIGHTS OF THE GOVERNMENT

The invention described herein may be manufactured and used by or for the Government of the United States for all governmental purposes without the payment of any royalty.

FIELD OF THE INVENTION

The present invention relates generally to fuel contamination and, more particularly, to methods and devices for evaluating fuel contamination.

BACKGROUND OF THE INVENTION

Effective monitoring of microbial growth in fuel is of great importance in prolonging the usable lifetime of vehicle and fuel systems and to ensure safety. Biocontamination may cause significant damage to a fuel system including, hydrocarbon degradation, changes in fuel properties and quality, corrosion, filter clogging, deactivation of fuel-water coalescers, coating degradation, inaccurate fuel level readings, decreased vehicle performance, and is often detected after the fuel system is compromised. Early detection of biofouling enables the use of cost-effective mitigation strategies that may reduce the contamination's impact on the fuel system. Thus, an early warning detection sensor to alert maintenance crew of biocontamination could save millions of dollars per year in repair costs over the lifetime of the vehicle and fuel system.

Conventionally, there has been no simple and reliable method for detecting microbes and biodeterioration in fuel. The methods used today are typically performed by highly trained scientists in laboratories. These laboratories are likely equipped with molecular-based instrumentation (such as PCR and sequencing instruments) that are quantitative in nature and do not differentiate between living and non-living microbes. Colony counting methods are quantitative and do not require expensive instrumentation; however, colony counting is very time consuming and only capable of detecting culturable bacteria, which may represent just 10% of all bacteria present within a fuel system.

Commercial kits are available, but are also cumbersome, inaccurate, and, at best, semi-quantitative. Some of these kits require multi-date culture growth for visual analysis or quantification of Adenosine Triphosphate ("ATP"). However, ATP levels are highly dependent on the growth stage of the microbe.

Other commercially-available kits use antibody-based detection methods. Antibodies are affected by degradation and are negatively influenced by the presence of fuel.

In view of the foregoing, a simplified, accurate method of detecting biocontamination in a short timeframe would be greatly useful in preserving fuel systems and minimizing repair and replacement costs due to biodeterioration. Heptameric (7-mer) phage library has a complexity of $1.28 \times 10^9$ peptide sequences and the dodecameric (12-mer) phage display library has a complexity of $4.1 \times 10^{15}$. From these exceedingly large numbers of random phages a mere 327 activity BREs against the disclosed targets were identified.

SUMMARY OF THE INVENTION

The present invention overcomes the foregoing problems and other shortcomings, drawbacks, and challenges of how to quickly, reliably, and accurately detect biocontamination within fuel systems. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention, a biorecognition element for rapid detection of biocontamination includes SEQ. ID No. 2 through SEQ. ID No. 24, SEQ. ID No. 26 through SEQ. ID No. 44, SEQ. ID No. 46 through SEQ. ID No. 57, SEQ. ID No. 59 through SEQ. ID No. 196 or SEQ. ID No. 198 through SEQ. ID No. 332. Preferably, in an embodiment of the present invention, a biorecognition element for rapid detection of biocontamination includes SEQ. ID No. 2, SEQ. ID No. 26, SEQ. ID No. 59, SEQ. ID No. 60, SEQ. ID No. 61, SEQ. ID No. 140, SEQ. ID No. 141 or SEQ. ID No. 142.

According to various aspects of the present invention, the biorecognition element may include one or more of a C-terminal, three-glycine plus cysteine linker cross-linking the biorecognition element to a quantum dot, an amine-functionalized quantum dot, and a reporter molecule. The reporter molecule may be fluorescent molecule, a chemiluminescent molecule, a colorimetric molecule, or a signal transducing nanomaterial.

Other embodiments of the present invention include a method of detecting biocontamination and include acquiring a sample and isolating microbes therefrom. The microbes are labeled with a first reporter conjugated to a biorecognition element. The biorecognition element is selected from the group consisting of SEQ. ID No. 2 through SEQ. ID No. 24, SEQ. ID No. 26 through SEQ. ID No. 44, SEQ. ID No. 46 through SEQ. ID No. 57, SEQ. ID No. 59 through SEQ. ID No. 196 or SEQ. ID No. 198 through SEQ. ID No. 332. Preferably, in an embodiment of the present invention, a biorecognition element for rapid detection of biocontamination includes SEQ. ID No. 2, SEQ. ID No. 26, SEQ. ID No. 59, SEQ. ID No. 60, SEQ. ID No. 61, SEQ. ID No. 140, SEQ. ID No. 141 or SEQ. ID No. 142.

According to some aspects of the present invention, isolating microbes from the fuel sample may include moving microbes from a fuel phase to an aqueous phase, drawing the aqueous phase from the fuel phase, and obtaining a microbe pellet from the aqueous phase by centrifugation. According to other aspects, isolating the microbes may include filtration.

Yet other embodiments of the present invention include a biocontamination assay kit. The kit includes a biorecognition element that is element selected from the group consisting of: SEQ. ID No. 2 through SEQ. ID No. 24, SEQ. ID No. 26 through SEQ. ID No. 44, SEQ. ID No. 46 through SEQ. ID No. 57, SEQ. ID No. 59 through SEQ. ID No. 196 or SEQ. ID No. 198 through SEQ. ID No. 332. Preferably, in an embodiment of the present invention, a biorecognition element for rapid detection of biocontamination includes SEQ. ID No. 2, SEQ. ID No. 26, SEQ. ID No. 59, SEQ. ID No. 60, SEQ. ID No. 61, SEQ. ID No. 140, SEQ. ID No. 141 or SEQ. ID No. 142. A C-terminal, three-glycine plus cysteine linker is on the biorecognition element. An amine-functionalized quantum dot is cross-linked to the cysteine linker, and a reporter molecule that is conjugated to the amine-functionalized quantum dot.

In some aspect of the present invention, the reporter molecule may be a fluorescent molecule, a chemiluminescent molecule, a colorimetric molecule, or a signal transducing nanomaterial.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Figure 1:
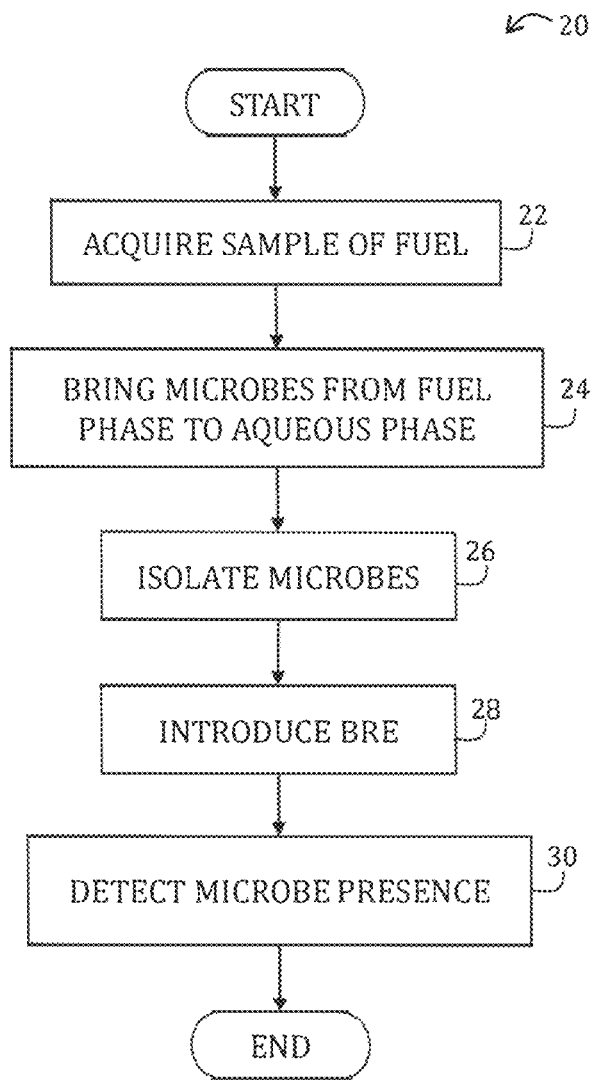
FIG. 1 is a flow chart illustrating a method of detecting fuel contamination according to one embodiment of the present invention is shown.
Figure 2:
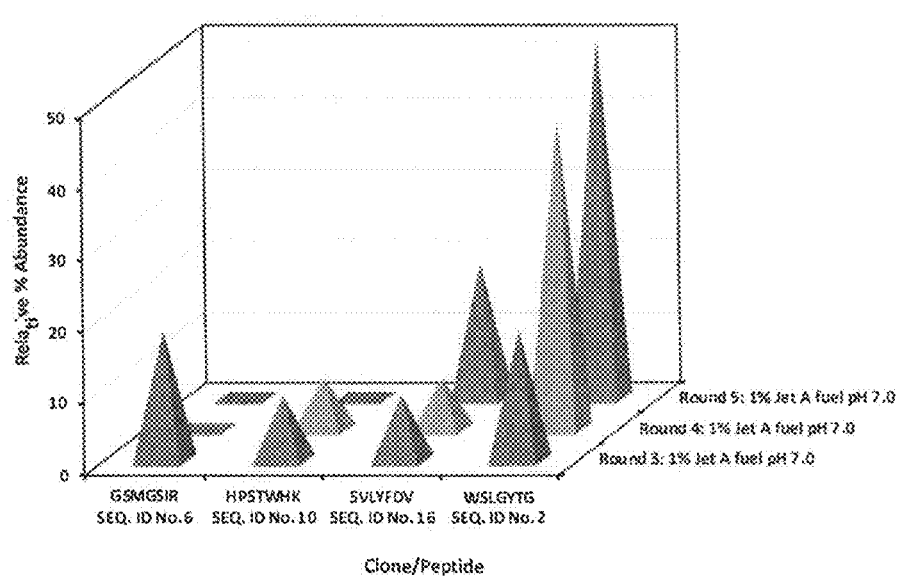
FIG. 2 is a graphical representation of ALK-P3 (SEQ. ID No. 1) binding peptides as a function of biopanning selection round, fuel and pH.
Figure 3:
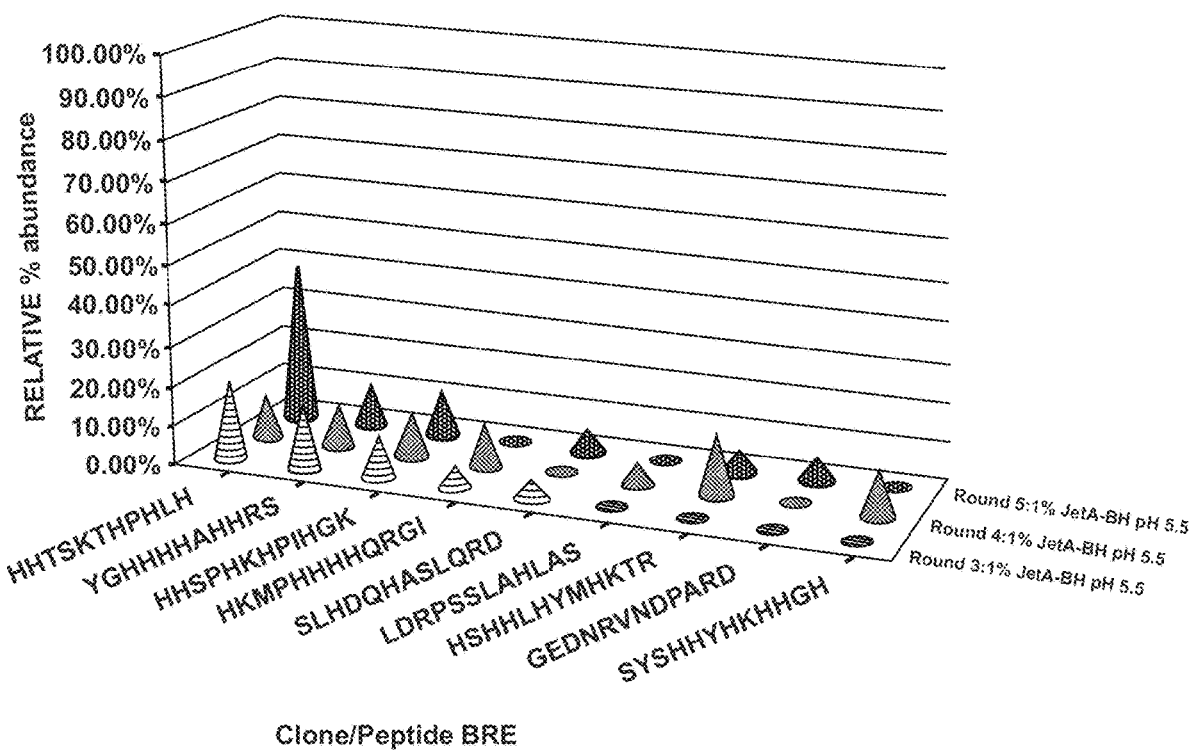
FIG. 3 is a graphical representation of LTA binding peptides distribution as a function of biopanning selection round, fuel and pH.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Fungi and Gram positive bacteria contaminate fuel and difficult to eradicate. Developing peptides that can detect such fuel degrading organisms that may be present in the fuel system and retain the binding activity in the presence of fuel has been a challenge in the past.

Biorecognition elements ("BREs") are short amino acid-based peptides or nucleic acid-based aptamers configured to mimic antibody-antigen interactions, and may be obtained by high throughput screening methods, such as systematic evolution of ligands by exponential enrichment ("SELEX") and phage display. Small, seven-to-twelve amino acid ("aa") peptides are ideal BREs and provide several benefits over other molecular probes, such as high chemical diversity, ease of synthesis and conjugation to the surface of a signal transducer, and high stability in harsh environments, such as fuel.

Peptide BREs are similar to antibody-antigen binding in that both have high affinity and specificity; however, unlike antibodies, short peptides do not require immunogenic antigens, post-translational modifications (such as disulfide bonds), and are not prone to batch variation. Moreover, peptide BREs are not prone to denaturation, have a longer shelf life, and are potentially reusable, all of which are unlike conventional large, multi-domain proteins and antibodies. Shorter, single-domain antibodies, also known as nanobodies, have even been shown to retain antigen binding activity in the presence of jet fuel. Tables 1 through 7 below provide additional detail concerning Applicants' BREs and thus supplement the sequence listings provided with the present specification. Tables 1 through 3 below disclose peptide BREs for fungi detection and Tables 4 through 7 below disclose peptide BREs for Gram-positive bacteria detection. BREs having SEQ. IDS Nos. 2-24, 26-44, 46-57, 59-196, and 198-332 are artificial and were obtained via biopanning.

TABLE 1

Target Protein: P450 Alkane Hydroxylase.
Target ID: ALK-P3 Target sequence: SEQ. ID No. 1
(YLPFNGGPRICVGQQFALAEASYAIVRL)

| BRE ID | BRE Sequence | SEQ. ID No. |
|---|---|---|
| 5ALK-23 | WSLGYTG | 2 |
| 4ALK15 | AYIHPIM | 3 |
| 3ALK-22 | FHHSNYG | 4 |
| 4ALK19 | GSFGYAW | 5 |
| 3ALK32 | GSMGSIR | 6 |
| 4ALK18 | GSQGDNG | 7 |
| 4ALK3 | HNFRTLV | 8 |
| 4ALK23 | HNNPPST | 9 |
| 4ALK30 | HPSTWHK | 10 |
| 4ALK28 | HSGGYMR | 11 |
| 3ALK2 | LFLPSVR | 12 |
| 3ALK39 | NPFVASS | 13 |
| 4ALK27 | RSLGYHG | 14 |
| 3ALK27 | SIVEDLV | 15 |
| 4ALK13 | SVLYFDV | 16 |
| 3ALK8 | TCMSEAC | 17 |
| 4ALK4 | TPTKTPW | 18 |
| 3ALK3 | VASPLFP | 19 |
| 4ALK1 | VLSAVPY | 20 |
| 4ALK17 | VWAGGYR | 21 |
| 3ALK-33 | WQTERIG | 22 |
| 3ALK5 | WSSSHM | 23 |
| 4ALK29 | YSSLGNS | 24 |

TABLE 2

Target Protein: Chitinase. Target ID: CHI-P1
Target sequence: SEQ. ID No. 25 (IPLCQQLGKILLSLGG)

| BRE ID | BRE Sequence | SEQ. ID No. |
|---|---|---|
| CHI3-13 | MPPHGDR | 26 |
| CHI3-6 | AITSRNA | 27 |
| CHI5-2 | AMTHMPN | 28 |
| CHI4-5 | DTMMRLN | 29 |
| CHI3-9 | ETFLITP | 30 |
| CHIS-10 | FAGTKDP | 31 |
| CHIS-13 | FSHKYVI | 32 |
| CHI3-3 | GDLYPTT | 33 |
| CHI4-16 | GTFLFSP | 34 |

TABLE 2-continued

Target Protein: Chitinase. Target ID: CHI-P1
Target sequence: SEQ. ID No. 25 (IPLCQQLGKILLSLGG)

| BRE ID | BRE Sequence | SEQ. ID No. |
|---|---|---|
| CHI4-9 | HLTSERL | 35 |
| CHI5-6 | MGIRAQA | 36 |
| CHI3-19 | MTTHMDY | 37 |
| CHI4-4 | NIHHLRF | 38 |
| CHI5-16 | NSLSPAG | 39 |
| CHI4-11 | QDAGLYW | 40 |
| CHI3-2 | QPHISPH | 41 |
| CHI3-20 | SQARPTI | 42 |
| CHI4-19 | SWSNWWE | 43 |
| CHI4-8 | TWTLARP | 44 |

TABLE 3

Target Protein: Carbohydrate Esterase.
Target ID: CES-P2
Target sequence:
SEQ. ID No. 45 (CPNTKLVASGYSQGGQLVH)

| BRE ID | BRE Sequence | SEQ. ID No. |
|---|---|---|
| CES3-8 | AGNTNNA | 46 |
| CES3-11 | AITSRNA | 47 |
| CES3-16 | APMVLLS | 48 |
| CES3-17 | FAGTKDP | 49 |
| CES4-9 | FPFTYLQ | 50 |
| CES4-2 | GLLTGHT | 51 |
| CES3-14 | HLTSERL | 52 |
| CES3-4 | HVTNGLW | 53 |
| CES3-9 | MIDLGAR | 54 |
| CES5-1 | MPTRVAP | 55 |
| CES3-3 | NSLSPAG | 56 |
| CES4-20 | TSFANSM | 57 |

TABLE 4

Gram positive Bacteria Fasciclin-Domain Protein
Target Protein: Gordonia-Fasciclin.
Target ID: Gor-Fasciclin1
Target sequence:
SEQ. ID No. 58 (ALSGKLNPQVNLVDTLNGGEFTVFA)

| BRE ID | BRE Sequence | SEQ. ID No. |
|---|---|---|
| 2Fas28 | TWTLARP | 59 |
| 4Fas6 | RSLGYTG | 60 |
| 3Fas22 | YVPEWVS | 61 |
| 2Fas6 | QGGISTT | 62 |

TABLE 4-continued

Gram positive Bacteria Fasciclin-Domain Protein
Target Protein: Gordonia-Fasciclin.
Target ID: Gor-Fasciclin1
Target sequence:
SEQ. ID No. 58 (ALSGKLNPQVNLVDTLNGGEFTVFA)

| BRE ID | BRE Sequence | SEQ. ID No. |
|---|---|---|
| 2Fas7 | MITGTQP | 63 |
| 2Fas8 | SMSLDDG | 64 |
| 2Fas9 | GILVPPT | 65 |
| 2Fas10 | FGPIGTW | 66 |
| 3Fas1 | YTDRFYM | 67 |
| 3Fas5 | MVLPPPA | 68 |
| 3Fas6 | WHRPFLL | 69 |
| 3Fas7 | SDDIRRN | 70 |
| 3Fas9 | FQTGDER | 71 |
| 3Fas10 | WSLGYTG | 72 |
| 3Fas14 | MLQSSLS | 73 |
| 3Fas15 | YTPLYAR | 74 |
| 3Fas16 | FSFGTRP | 75 |
| 3Fas17 | KSSWEFA | 76 |
| 3Fas18 | VTLVNGI | 77 |
| 4Fas1 | ISFTPKT | 78 |
| 4Fas3 | LQAMPNR | 79 |
| 4Fas4 | FPGSSPK | 80 |
| 4Fas5 | TKTPHIH | 81 |
| 4Fas10 | VSHVIND | 82 |
| 4Fas12 | HVTNGLW | 83 |
| 4Fas13 | HILNWPT | 84 |
| 4Fas14 | NNWFSFD | 85 |
| 4Fas15 | YWTSGQL | 86 |
| 4Fas16 | GRNLIEM | 87 |
| 4Fas18 | GSFGYTR | 88 |
| 4Fas20 | CDFRSIK | 89 |
| 5Fas2 | WHWQTRG | 90 |
| 5Fas4 | STALPFR | 91 |
| 5Fas14 | YIPGTVP | 92 |
| 5Fas17 | SMSISSR | 93 |
| 5Fas20 | WSWHHSG | 94 |
| 2Fas22 | EHVEPSR | 95 |
| 2Fas23 | NQFSLSQ | 96 |
| 2Fas24 | YKFGQQG | 97 |
| 2Fas26 | HYGTYNV | 98 |
| 2Fas27 | TGYPLES | 99 |
| 2Fas29 | FTTFTSN | 100 |
| 2Fas30 | SWPSRIP | 101 |
| 3Fas23 | YPDYLAR | 102 |
| 3Fas24 | NHWVQYF | 103 |
| 3Fas25 | KIVHRLY | 104 |
| 3Fas26 | INQTQLT | 105 |
| 3Fas27 | YTQGHLL | 106 |
| 3Fas30 | DTKYMTS | 107 |
| 3Fas31 | MLLGETG | 108 |
| 3Fas32 | NMLHALY | 109 |
| 3Fas33 | LPQFQNC | 110 |
| 3Fas34 | LPQVQTC | 111 |
| 3Fas35 | SENPHFK | 112 |
| 3Fas36 | NYYSAKT | 113 |
| 3Fas37 | NNDMPAP | 114 |
| 3Fas38 | HFLNAQH | 115 |
| 3Fas39 | SWWRSEL | 116 |
| 3Fas40 | LQYSTRL | 117 |
| 4Fas21 | SSYIDYR | 118 |
| 4Fas22 | NDSKTPS | 119 |
| 4Fas23 | HGDHVSH | 120 |
| 4Fas24 | YSSLWLQ | 121 |
| 4Fas25 | YHNQKSW | 122 |
| 4Fas26 | GKLPPRY | 123 |
| 4Fas27 | FPLRAPS | 124 |
| 4Fas28 | IGALDAR | 125 |
| 4Fas29 | KPMLFFG | 126 |
| 4Fas30 | STMYTVY | 127 |
| 4Fas31 | LHASIPP | 128 |
| 4Fas32 | HLSLAMR | 129 |
| 4Fas33 | LSWPKFL | 130 |
| 4Fas38 | QGDQESR | 131 |
| 4Fas39 | ALSSILT | 132 |
| 4Fas40 | SVALGAY | 133 |
| 5Fas22 | RSLGYPG | 134 |

TABLE 4-continued

Gram positive Bacteria Fasciclin-Domain Protein
Target Protein: Gordonia-Fasciclin.
Target ID: Gor-Fasciclin1
Target sequence:
SEQ. ID No. 58 (ALSGKLNPQVNLVDTLNGGEFTVFA)

| BRE ID | BRE Sequence | SEQ. ID No. |
| --- | --- | --- |
| 5Fas25 | FHGIPSV | 135 |
| 5Fas26 | WSLRYTR | 136 |
| 5Fas27 | WSLGYTW | 137 |
| 5Fas30 | WSHGYTG | 138 |
| 5Fas32 | LESFYTG | 139 |

TABLE 5

Gram Positive Bacteria Lipoteichoic Acid (LTA)
Target ID: LTA
Cell target (cell wall) Lipoteichoic Acid
Target: Poly (glycerol-phosphate) units,
substituted with d-alanine and/or sugars, and
covalently linked to β-gentiobiosyldiacylglycerol

| BRE ID | BRE Sequence | SEQ. ID No. |
| --- | --- | --- |
| 3Lip21 | WTNPYLALDHPM | 140 |
| 4Lip23 | WKNPYLALDHPM | 141 |
| 3Lip52 | WRNPYLALDHPM | 142 |
| 3LTA2 | KHHHVHH | 143 |
| 3LTA3 | HHHHRPH | 144 |
| 3LTA18 | HHHHHTR | 145 |
| 5LTA16 | HRHHWHH | 146 |
| 5LTA19 | RAMDRMP | 147 |
| 3Lip1 | WPNHHHHPRAHT | 148 |
| 3Lip2 | HHTSHKTHPHLH | 149 |
| 3Lip3 | YGHHHHAHHIRS | 150 |
| 3Lip4 | HHSPHKHPIHGK | 151 |
| 3Lip5 | HHSHHVHQGMRP | 152 |
| 3Lip7 | HSHHLPYMHKTR | 153 |
| 3Lip9 | VDLNPSGRFQIS | 154 |
| 3Lip10 | HHHHSIRGHSGS | 155 |
| 3Lip11 | HSHGHLRHHMVN | 156 |
| 3Lip12 | SLHDQHASLQRD | 157 |
| 3Lip13 | HKMPHHHHQRGI | 158 |
| 3Lip15 | ESGRGPDEGKSP | 159 |
| 3Lip19 | ALHGHHRWHKTH | 160 |
| 4Lip1 | HSHHLHYMHKTR | 161 |
| 4Lip2 | HIGHHHHSKMRT | 162 |
| 4Lip3 | SVRHVHHSHWS | 163 |
| 4Lip4 | HHHGERLHHHSY | 164 |
| 4Lip5 | GHHVHHKHPVNH | 165 |
| 4Lip6 | SQHHHHIKHYMT | 166 |
| 4Lip9 | LDRPSSLAHLAS | 167 |
| 4Lip15 | SYSHHYHKHHGH | 168 |
| 4Lip17 | AHFCTASHCHAR | 169 |
| 5Lip5 | NPHHHRNQHHSI | 170 |
| 5Lip13 | GEDNRVNDPAR | 171 |
| 5Lip14 | ARHHHSHVHWLR | 172 |
| 5Lip15 | HHHHRLNTSSKH | 173 |
| 5Lip16 | GYKHHHRTHTTA | 174 |
| 3Lip30 | GNNPLHVHHDKR | 175 |
| 3Lip34 | LAPTYIMWGTSS | 176 |
| 3Lip35 | DYHDPSLPTLRK | 177 |
| 3Lip38 | AHDPFPMRLLRA | 178 |
| 3LTA21 | DMKARVA | 179 |
| 3LTA23 | SIAHNTM | 180 |
| 3LTA24 | LVTVPRS | 181 |
| 3LTA25 | GDMLTLR | 182 |
| 3LTA26 | HSSTVTI | 183 |
| 3LTA28 | FALTPPP | 184 |
| 3LTA29 | QNNIHTP | 185 |
| 3LTA30 | QAHWLRE | 186 |
| 3LTA31 | TMIDANR | 187 |
| 3LTA32 | GSFIIHT | 188 |
| 3LTA33 | YGTSLSR | 189 |
| 3LTA34 | HGKILLT | 190 |
| 3LTA35 | GPYSVLA | 191 |
| 3LTA37 | YSLSLPE | 192 |
| 3LTA38 | GCKRYTG | 193 |
| 4LTA24 | WSLGYTG | 194 |
| 4LTA27 | WVMNHPQ | 195 |
| 4LTA28 | RLLGHTR | 196 |

TABLE 6

Gram positive Bacteria Dicarboxylate/
amino acid:cation symporter
Target Protein: Dicarboxylate/
amino acid:cation symporter.
Target ID: Nocar 1 Target sequence:
SEQ. ID No. 197 (NVNGDTMVALLVAHGAGEIDRDVY)

| BRE ID | BRE Sequence | SEQ. ID No. |
|---|---|---|
| 3Noc1 | SGFPVKD | 198 |
| 3Noc2 | DPLHMKK | 199 |
| 3Noc5 | SDFFTTS | 200 |
| 3Noc6 | FDIASPS | 201 |
| 3Noc7 | TSQVNHD | 202 |
| 3Noc8 | NVLSPPF | 203 |
| 3Noc10 | YTLPKAR | 204 |
| 3Noc12 | LLNPWTH | 205 |
| 3Noc13 | EHAIQYP | 206 |
| 3Noc14 | SHVLSVA | 207 |
| 3Noc16 | HDSVHFD | 208 |
| 3Noc17 | VPWPMSI | 209 |
| 3Noc19 | VPRTAFW | 210 |
| 3Noc20 | MTDFVFS | 211 |
| 4Noc2 | AKLVSRV | 212 |
| 4Noc5 | IPWYWYL | 213 |
| 4Noc6 | VIHRPMT | 214 |
| 4Noc8 | YLTDSWD | 215 |
| 4Noc9 | TPRSSHP | 216 |
| 4Noc10 | GCAPYKR | 217 |
| 4Noc11 | KTSLESI | 218 |
| 4Noc12 | WSLGYTG | 219 |
| 4Noc13 | KLPQIAS | 220 |
| 4Noc14 | SHNTWMP | 221 |
| 4Noc17 | NLAPFTF | 222 |
| 5Noc19 | YGDMPRF | 223 |
| 3Nocar1 | GMHGKCYGRELC | 224 |
| 3Nocar2 | SVDGWLEPPTST | 225 |
| 3Nocar3 | QVNGLGERSQQM | 226 |
| 3Nocar4 | RDYHPRDHTATW | 227 |
| 3Nocar5 | TYAMLARVDGLS | 228 |
| 3Nocar8 | GNNPLHVHHDKR | 229 |
| 3Nocar9 | DYHDPSLPTLRK | 230 |
| 3Nocar11 | SGLNYSWPEVKN | 231 |
| 3Nocar12 | VPPEGPMERYIG | 232 |
| 3Nocar13 | HSHHRHHHLNNR | 233 |
| 4Nocar5 | SLLAERQFNSKP | 234 |
| 4Nocar9 | YGHHHHAHHIRS | 235 |
| 4Nocar11 | YPVETHLSARVI | 236 |
| 3Nocar21 | RDYHPRDHTATW | 237 |
| 3Nocar22 | DYHDPSLLPMRK | 238 |
| 3Nocar24 | RDHHPRDHTVRR | 239 |
| 3Nocar32 | KPHWKNQDGLMI | 240 |
| 3Nocar38 | WENVPITQQRPR | 241 |
| 4Nocar25 | KVYHEGLSMKKH | 242 |
| 4Nocar35 | DNHDPSLPPDKK | 243 |
| 4Nocar38 | DYHDPSLPPQKK | 244 |
| 5Nocar21 | KLWSIPTNFLLP | 245 |
| 5Nocar24 | SLEYPGERTQRK | 246 |
| 5Nocar25 | KPGFDVCAWWRC | 247 |
| 5Nocar30 | LSSGSKFAYAAK | 248 |
| 3Noc21 | NIHRPIL | 249 |
| 3Noc23 | PSLITPV | 250 |
| 3Noc24 | LTSLDTY | 251 |
| 3Noc26 | EVIGTPK | 252 |
| 3Noc27 | TIWDSFT | 253 |
| 3Noc28 | RFPTSFD | 254 |
| 3Noc29 | TYPTLTI | 255 |
| 3Noc30 | SVLRMLN | 256 |
| 3Noc32 | HSLIMPA | 257 |
| 3Noc33 | YPLGLTR | 258 |
| 3Noc38 | MLSLPQQ | 259 |
| 3Noc39 | NLYPPLS | 260 |
| 4Noc22 | HQVAFKI | 261 |
| 4Noc23 | WHYPLSV | 262 |
| 4Noc26 | QSIPSYW | 263 |
| 4Noc32 | YPPLAGH | 264 |
| 4Noc33 | WPTRLSE | 265 |
| 4Noc34 | RSHGYSG | 266 |
| 4Noc35 | RSQGYHG | 267 |
| 4Noc37 | NNIVARW | 268 |

TABLE 6-continued

Gram positive Bacteria Dicarboxylate/
amino acid:cation symporter
Target Protein: Dicarboxylate/
amino acid:cation symporter.
Target ID: Nocar 1 Target sequence:
SEQ. ID No. 197 (NVNGDTMVALLVAHGAGEIDRDVY)

| BRE ID | BRE Sequence | SEQ. ID No. |
| --- | --- | --- |
| 4Noc39 | GNLSSAA | 269 |
| 5Noc23 | THSTPSL | 270 |
| 5Noc32 | VVPTRVY | 271 |
| 5Noc34 | HMPCLLL | 272 |
| 5Noc35 | GTIYWNS | 273 |
| 5Noc37 | ASWAPMP | 274 |
| 5Noc39 | DLGPRPL | 275 |
| 5Noc40 | TLTSGVL | 276 |
| 3Nocar48 | LELDPSQLYAHH | 277 |
| 4Nocar42 | GVHSVFAPLTPN | 278 |
| 4Nocar44 | SSSGVMHGPPVL | 279 |
| 4Nocar47 | TAKYLPMRPGPL | 280 |
| 4Nocar53 | SEVLTFAWWRC | 281 |
| 4Nocar57 | HHLRIPYALDQT | 282 |
| 4Nocar58 | KPGFDVCAWRRC | 283 |
| 5Nocar48 | KLGFDVCAWRRW | 284 |

TABLE 7

Gram-positive LPXTG cell wall anchor.
Target sequence:
Target ID: LPxTG Cell target (cell wall)
Target in cell wall: LPxTG x = any amino acid

| BRE ID | BRE Sequence | SEQ. ID No. |
| --- | --- | --- |
| R3LP14 | TSWRHVE | 285 |
| R3LP37 | IVNQGLP | 286 |
| R3LP6 | QSPTHPS | 287 |
| R3LP22 | RSLGYTG | 288 |
| R3LP29 | LKTGDLR | 289 |
| R3LP7 | SDRILYL | 290 |
| R3LP30 | KDLPVTP | 291 |
| R3LP18 | SLLSFDR | 292 |
| R3LP16 | QSNAVRI | 293 |
| R3LP4 | HSRLPTP | 294 |
| R3LP32 | SVQFIHD | 295 |
| R3LP9 | TQFLEMV | 296 |
| R3LP3 | HVFALVH | 297 |
| R3LP19 | GNLINID | 298 |
| R3LP26 | EFVMYSR | 299 |
| R3LP31 | KDLPVTP | 300 |
| R3LP20 | GIIGDTP | 301 |
| R3LP2 | TCANCWP | 302 |
| R3LP11 | GMKPHAY | 303 |
| R3LP12 | STVHKQI | 304 |
| R3LP28 | LMTDDPR | 305 |
| R3LP5 | NGTTIYS | 306 |
| R3LP21 | YSFGDWR | 307 |
| R3LP39 | WSLGYTG | 308 |
| R3LP13 | VGSPLTP | 309 |
| R3LP17 | WTQYYPW | 310 |
| R3LP40 | MNYYDAY | 311 |
| R3LP8 | VPYPTIR | 312 |
| R3LP25 | MDLSVGV | 313 |
| R3LP38 | EGFSHWS | 314 |
| R3LP1 | SYQTSTS | 315 |
| R5LP3 | HKLNTPP | 316 |
| R5LP11 | HRHHHSH | 317 |
| R5LP12 | HHHHRPH | 318 |
| R5LP5 | HKHLHHH | 319 |
| R5LP6 | HKHGHHH | 320 |
| R5LP7 | HHKHVHR | 321 |
| R5LP10 | HHHHHTR | 322 |
| R5LP37 | STTGTQY | 323 |
| R4LP1 | DFAQWYL | 324 |
| R4LP4 | VHVQATS | 325 |
| R4LP8 | ESGRMAH | 326 |
| R4LP12 | DITRFLL | 327 |
| R4.1LP11 | WSIVNAG | 328 |
| R4.1LP10 | GSLGYTR | 329 |
| R4.1LP18 | TSDSEAR | 330 |
| R4.1LP3 | HYHCNPW | 331 |
| R4.1LP11 | WSIVNAG | 332 |

With the foregoing, and turning now to FIG. 1, a method 20 of detecting fuel contamination is shown. At start, a sample of fuel for testing is acquired (Block 22). The sample may include a fuel phase, an aqueous phase, or both and may be acquired from fuel dispensers, fuel tanks, pipelines, and so forth. The fuel may be any liquid type fuel, such as jet fuel, diesel, biodiesel, kerosene, gasoline with or without alcohol content (such as biofuels), sustainable fuels, fuel blends, and so forth; however, embodiments of the present invention may also be suitable for detecting microbial contamination in hydraulic fluids, lubricants, synthetic and natural oils, hydrocarbon-based plastics, fatty acid methyl esters, solvents, process water and so forth. The sample size may vary, but should be sufficient large to capture the biodiversity within the fuel sample—for example, 0.1 L to 1 L may be sufficient in some instances.

The fuel sample may then be prepared for collecting microbes contained therein. According to the illustrative embodiment of the present invention, phosphate-buffered saline ("PBS") buffer (pH 7.2) may be added to the sample to bring microbes in the fuel phase into the PBS buffer/aqueous phase (Block 24). The PBS buffer/aqueous phase may be transferred from the sample and centrifuged (such as at 10,000 RPMs) to yield a microbe pellet (Block 26). Alternatively, although not specifically shown, a filter may be used to separate and recover microbes from fuel samples to allow direct detection on the filter or to recover the microbes to a solution for detection as described above. A 0.1 µm to 0.45 µm diameter filter made of cellulose, polyvinylidene difluoride ("PVDF"), or other material, or a filter made of graphene oxide nanomaterial, may be used to filter an aliquot of fuel (i.e., fuel, water, or fuel and water) while retaining and separating microbes out of the fuel for direct detection onto the filter with BRE-QDs. Alternatively, microbes may be recovered from the filter into an aqueous solution by agitation or vortex for detection as described above.

With the microbes isolated, and using a biorecognition element selected, hereinafter referred to as BRE" from SEQ. ID No. 2 through SEQ. ID No. 24, SEQ. ID No. 26 through SEQ. ID No. 44, SEQ. ID No. 46 through SEQ. ID No. 57, SEQ. ID No. 59 through SEQ. ID No. 172, and SEQ. ID No. 174 through SEQ. ID No. 308, or preferably, SEQ. ID No. 2, SEQ. ID No. 26, SEQ. ID No. 59, SEQ. ID No. 60, SEQ. ID No. 61, SEQ. ID No. 116, SEQ. ID No. 117 or SEQ. ID No. 118, microbes with the specified surface protein or polysaccharide may be detected. In that regardBREs—may be conjugated to reporter such as a fluorescent, chemiluminescent, and colorimetric molecules or signal transducing nanomaterials for optical detection of the target without altering the antigen-binding capacity and biorecognition activity of the BRE. Thus, according to some embodiments of the present invention, peptide BREs biofunctionalized quantum dot ("QD") may be used as reporter fluorophores. While other embodiments may utilize conventional chemical dyes, QDs may be used in lieu thereof to provide improved brightness and stability against photo-bleaching. QDs broad absorption spectra allow for utilization of a single excitation source; the narrow symmetrical emission spectra, size-dependent quantum yields, and large Stokes shifts make QDs excellent reporter fluorophores for multiplexed detection of different microorganisms.

The resulting BRE-QD conjugates may be used as labeling reagents in a lateral flow assay for the quantitative detection of Gram-Positive bacteria and fungiin the presence of fuel. The assay specificity and limit of detection ("LOD") was determined and its application in the detection of bacteria and fungi in contaminated fuel samples from field tanks was demonstrated.

The BRE-QD conjugates may then be introduced to the microbes (Block 28). While the amount of BRE-QD introduced to the isolated microbe may vary, using the exemplary 0.1 L to 1 L fuel sample noted above, 0.1 mL of 1.5 µM Peptide BRE-QD solution in PBS at room temperature for 15 to 30 min may be used to label the microbes. If desired or necessary, the microbes may be washed and resuspended prior to detection.

Detection of the microbes depends on the labeling embodiment used (Block 30). For instance, using the BRE-QD embodiment, presence and amount of microbes may be detected measuring fluorescence (emission spectra) with a fluorometer. According to one specific embodiment, a Cary Eclipse Fluorimeter at 330 nm excitation and fluorescence collection at 545 nm or any other may be used.

According to other embodiments of the present invention, the peptide BREs may be to biofunctionalize a gamut fluorescent and chemiluminescent molecules (e.g., dyes and particles) for fluorescent and colorimetric microbial detection. The ordinarily-skilled artisan having the benefit of the disclosure made herein would readily appreciate how such biofunctionalized BREs may be detected and reported.

Moreover, the peptide BREs may be used to biofunctionalize optical transducers (such as antenna resonators or photonic gratings), electrical and electro-chemical transducers (such as graphene-based field effect transistors, quartz crystal microbalance), graphene oxide-based sensing materials, and so forth to provide real-time detection of microbial contamination of fuel supplies and tanks.

This is paragraph forty-two of this specification. In this paragraph forty-two, Applicants disclose a biorecognition element for rapid detection of microbial biocontamination, the biorecognition element comprising: SEQ. ID No. 2 through SEQ. ID No. 24, SEQ. ID No. 26 through SEQ. ID No. 44, SEQ. ID No. 46 through SEQ. ID No. 57, SEQ. ID No. 59 through SEQ. ID No. 196 or SEQ. ID No. 198 through SEQ. ID No. 332.

This is paragraph forty-three of this specification. In this paragraph forty-three, Applicants disclose the biorecognition element of paragraph forty-two, the biorecognition element comprising: SEQ. ID No. 2, SEQ. ID No. 26, SEQ. ID No. 59, SEQ. ID No. 60, SEQ. ID No. 61, SEQ. ID No. 140, SEQ. ID No. 141 or SEQ. ID No. 142.

This is paragraph forty-four of this specification. In this paragraph forty-four, Applicants disclose the biorecognition element of paragraph forty-two, further comprising: a C-terminal, three-glycine plus cysteine linker configured to cross-link to an amine-functionalized quantum dot.

This is paragraph forty-five of this specification. In this paragraph forty-five, Applicants disclose the biorecognition element of paragraph forty-four, further comprising: an amine-functionalized quantum dot cross-linked to the cysteine linker; and a reporter molecule conjugated to the amine-functionalized quantum dot.

This is paragraph forty-six of this specification. In this paragraph forty-six, Applicants disclose the biorecognition element of paragraph forty-five, wherein the reporter molecule is a fluorescent molecule, a chemiluminescent molecule, a colorimetric molecule, or a signal transducing nanomaterial.

This is paragraph forty-seven of this specification. In this paragraph forty-seven, Applicants disclose the biorecognition element of paragraph forty-two, wherein the microbial biocontamination is in a fuel phase or an aqueous phase of a fuel sample.

This is paragraph forty-eight of this specification. In this paragraph forty-eight, Applicants disclose a method of detecting biocontamination, the method comprising: labeling isolating microbes from a fuel sample with a first reporter, wherein the first reporter is conjugated to a biorecognition element selected from the group consisting of: SEQ. ID No. 2 through SEQ. ID No. 24, SEQ. ID No. 26 through SEQ. ID No. 44, SEQ. ID No. 46 through SEQ. ID No. 57, SEQ. ID No. 59 through SEQ. ID No. 196 or SEQ. ID No. 198 through SEQ. ID No. 332.

This is paragraph forty-nine of this specification. In this paragraph forty-nine, Applicants disclose the method of paragraph forty-eight, wherein, said biorecognition element is selected from the group consisting of: SEQ. ID No. 2, SEQ. ID No. 26, SEQ. ID No. 59, SEQ. ID No. 60, SEQ. ID No. 61, SEQ. ID No. 140, SEQ. ID No. 141 and SEQ. ID No. 142.

This is paragraph fifty of this specification. In this paragraph fifty, Applicants disclose the method of paragraph forty-eight, wherein the sample is a fuel sample and the method of isolating the isolated microbes comprises:
  moving microbes from a fuel phase of the fuel sample to an aqueous phase of the fuel sample;
  drawing the aqueous phase from fuel phase; and
  obtaining a microbe pellet by centrifugation.

This is paragraph fifty-one of this specification. In this paragraph fifty-one, Applicants disclose the method of paragraph forty-eight, wherein isolating microbes from the fuel sample comprises: filtering the microbes from a fuel phase of the fuel sample, an aqueous phase of the fuel sample, or both.

This is paragraph fifty-two of this specification. In this paragraph fifty-two, Applicants disclose the method of paragraph forty-eight, wherein the biorecognition element further comprises:
  a C-terminal, three-glycine plus cysteine linker; and
  an amine-functionalized quantum dot cross-linked to the cysteine linker,
wherein the reporter is conjugated to the amine-functionalized quantum dot.

This is paragraph fifty-three of this specification. In this paragraph fifty-three, Applicants disclose the method of paragraph forty-eight, wherein the first reporter is a fluorescent molecule, a chemiluminescent molecule, a colorimetric molecule, or a signal transducing nanomaterial.

This is paragraph fifty-four of this specification. In this paragraph fifty-four, Applicants disclose the method of paragraph forty-eight, comprising:
labeling the microbes with a second reporter, wherein the second reporter is conjugated to a biorecognition element selected from the group consisting of: SEQ. ID No. 2 through SEQ. ID No. 24, SEQ. ID No. 26 through SEQ. ID No. 44, SEQ. ID No. 46 through SEQ. ID No. 57, SEQ. ID No. 59 through SEQ. ID No. 196 or SEQ. ID No. 198 through SEQ. ID No. 332.

This is paragraph fifty-five of this specification. In this paragraph fifty-five, Applicants disclose the a biocontamination assay kit comprising:
  a biorecognition element selected from the group consisting of: SEQ. ID No. 2 through SEQ. ID No. 26, SEQ. ID No. 22 through SEQ. ID No. 44, SEQ. ID No. 46 through SEQ. ID No. 57, SEQ. ID No. 59 through SEQ. ID No. 196 or SEQ. ID No. 198 through SEQ. ID No. 332;
  a C-terminal, three-glycine plus cysteine linker on the biorecognition element;
  an amine-functionalized quantum dot cross-linked to the cysteine linker; and a reporter molecule conjugated to the amine-functionalized quantum dot.

This is paragraph fifty-six of this specification. In this paragraph fifty-six, Applicants disclose the biocontamination assay kit of paragraph fifty-five, wherein said biorecognition element is selected from the group consisting of: SEQ. ID No. 2, SEQ. ID No. 26, SEQ. ID No. 59, SEQ. ID No. 60, SEQ. ID No. 61, SEQ. ID No. 140, SEQ. ID No. 141 and SEQ. ID No. 142.

This is paragraph fifty-seven of this specification. In this paragraph fifty-seven, Applicants disclose the biocontamination assay kit of paragraph fifty-five, comprising: a filter permeable to liquid and configured to retain microbes.

This is paragraph fifty-eight of this specification. In this paragraph fifty-eight, Applicants disclose the biocontamination assay kit of paragraph fifty-seven, wherein the liquid is a fuel.

This is paragraph fifty-nine of this specification. In this paragraph fifty-nine, Applicants disclose the biocontamination assay kit of paragraph fifty-five, wherein the reporter molecule is a fluorescent molecule, a chemiluminescent molecule, a colorimetric molecule, or a signal transducing nanomaterial.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1

Highly conserved N-terminal biotinylated synthetic peptides of target proteins and biotinylated Lipoteichoic Acids (LTA) were used for solution biopanning screening of a commercially-available M13 bacteriophage library displaying heptameric peptides at the N-terminal of P3 coat protein. Solution-phase biopanning provided the benefit of including the availability of all of the target peptide for interaction with the potential peptide binder with lessened likelihood of isolating unspecific peptides that might bind to the capture element used to purify the phage-antigen complex (i.e., magnetic or protein G beads Generally, solution-phase biopanning was carried out as described by the manufacturer (New England Biolabs, Ipswich, Mass.) with some modifications, including the changing of pH from 7.0 to 5.5 and 8.5 and adding 1% v/v of Jet A fuel. The first round of selection was carried out by diluting Ph.D.-7 or Ph.D.-12 bacteriophage library 100-fold in 0.1% Tris buffer saline plus Tween 20 (0.1% TBST) at the appropriate pH for selection plus fuel. Subsequently, the phage library was incubated with 1 µg of N-terminal biotinylated target (SEQ. ID No. 1: YLPFNGGPRICVGQQFA-LAEASYAIVRL); SEQ. ID No. 25:IPLCQQLGKILL-SLGG); SEQ. ID No. 45:CPNTKLVASGYSQGGQLVH; SEQ. ID No. 58:ALSGK- LNPQVNLVDTLNGGEFTVFA; Target ID: LTA, Lipoteichoic Acid; SEQ. ID No. 173: NVNGDTMVALLVAHGAGEIDRDVY); Target ID: LPXTG, cell wall anchor. Target sequence) for 1 hr at 25° C. Phage-target complexes were captured with 50 µL of streptavidin magnetic microbeads, unbound phages were removed, and the pellet sample washed 10-times with 1 mL of 1× Tris buffer saline ("TBS") plus 0.05% TBST to remove weakly bound phage particles. Bound bacteriophages were eluted from the beads by lowering the pH (0.2 M Glycine-HCl, pH 2.2) while rotating gently for 10 min at 25° C. After neutralization with 1M Tris-HCl, pH 9.1, eluted phages were amplified by infection of *E. coli* strain ER 2738 grown in Luria-Bertani ("LB") broth medium until early-log phase (OD600 0.1-0.5). Titer of the amplified phage (more than $10^{10}$ pfu/mL) was determined by infection into *E. coli* ER2738 and subsequent growth in selective medium containing X gal/IPTG. Amplified phages from round 1 were pre-cleared with streptavidin-coated magnetic microbeads (50 µL) to further remove non-specific binders and then used as the input phage for round 2 of selection. Enrichment of the bacteriophage pool was achieved by performing 4 rounds of selection under the appropriate pH plus jet fuel condition. Genomic DNA from individual clones was sequenced by GenScript (Piscataway, N.J.).

Phage-target complexes were captured with streptavidin coated magnetic microbeads; non-binding phages were removed by a series of washes with 0.1% Tween-TBS, pH 7.

Phages with BREs specific against target were eluted by lowering pH to 2, neutralization with Glycine Buffer (pH 9), infection of the *E. coli* ER2738 host, and subsequent amplification. The amplified phage pool was isolated by precipitation with PEG/NaCl and titered to determine phage concentration.

Recombinant phage clones were selected using X-Gal/IPTG, which produced a blue color on phage infected *E. coli* colonies. After the amplification of multiple phage isolates carrying a single heptapeptide sequence (i.e., monoclonal phages), genomic DNA was isolated and sequenced to determine the aa sequences of the peptide BREs. Isolated monoclonal phages were sequenced after each round of selection. After four rounds of selection, the phage pool was enriched for target-binding phages with specific sequences. To increase the specificity phage-displayed peptides for testing fuel, the BRE selection process was performed using fuel at different pHs including non-physiological conditions (e.g., pH 5.5 or pH 8.5). The binding of phages displaying specific peptide BREs to the target was assessed by Western blot analysis. Monoclonal target-specific bacteriophages were incubated with biotinylated target peptide epitope under conditions similar to those used in biopanning. The resulting phage-target complexes were recovered using streptavidin-coated magnetic beads, and the phage-target complexes were resolved via SDS-PAGE and detected by Western blot using antibodies against the M13 phage capsid and the biotin molecule attached to the specific target. Western blotting was performed by preparing a 200 µL solution with each of the phage clones at a concentration of $1 \times 10^{11}$ pfu/mL in 1xTBS, pH 7.5. Then, 10 µL of biotinylated target peptide of concentration 1 mg/mL was added to each phage solution and incubated at 25° C. for 1 hr. Phage-biotin target complexes were captured and pull-down with 25 µL of streptavidin-coated beads, and the captured complexes washed five times with 1xTBST. The pelleted complexes were re-suspended in 20 µL of 2x Laemmli Buffer, heated to 95° C. for 5 min, and resolved in a 14% SDS-PAGE gel. Proteins were blotted to a nitrocellulose membrane and blocked with TBST containing 5% BSA. To detect phages, a 1:2000 dilution of rabbit anti-M13 phage antibody (primary antibody) followed by a 1:5000 dilution of alkaline phosphatase (AP)-conjugated goat anti-rabbit antibody was used. For detection of biotinylated target, a 1:2000 dilution of AP-conjugated goat anti-biotin antibody was used. For colorimetric visualization, BCIP/NBT reagent was used. M13 phage and biotinylated target were used as positive controls using 10 µL of $9 \times 10^{12}$ pfu/mL wild type M13 phage in 10 µL 2x Laemmli Buffer and 20 µL of 1 mg/mL target peptide-biotin in 20 µL 2x Laemmli Buffer per well, respectively.

Figure 4:
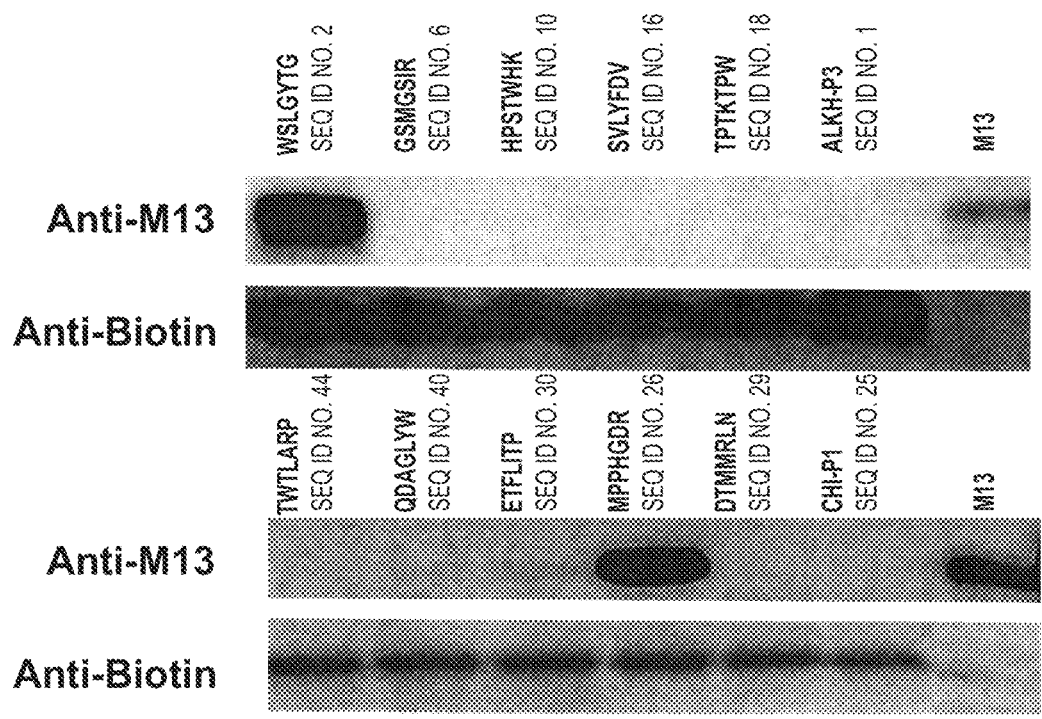
FIG. 4 is an image captured from a Western blot analysis showing specific binding of peptide SEQ. ID No. 2 and SEQ. ID No. 26 to ALK-P3 (SEQ. ID No. 1) and CHI-P1 (SEQ. ID No. 25) targets.
Figure 5:
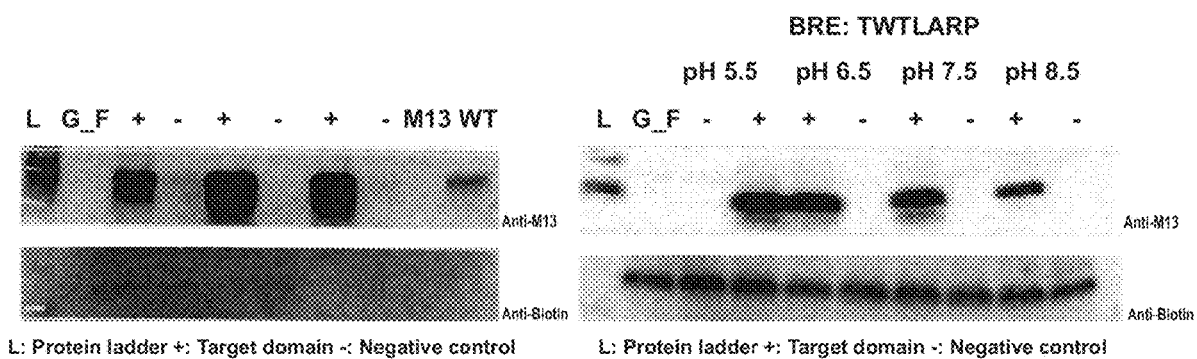
FIG. 5 is an image captured from a Western blot analysis showing specific binding of peptide SEQ. ID No. 59, SEQ. ID No. 60, SEQ. ID No. 61 to Gor-Fasciclin (SEQ. ID No. 58) target.

Monoclonal target-specific phages were shown to bind specifically to the biotinylated target peptide, and both the phage and target were detected in immunoblots (FIG. 4 & FIG. 5). When phages with specificity for BSA were used against the—target, signal was not detected in the immunoblots, which suggests that complexing specificity was due to the presence of target-specific—peptide BREs and not due to non-specific binding of M13 phage capsid proteins and non-target library peptides (Please cite the previous patent or paper).

Example 2

Figure 6:
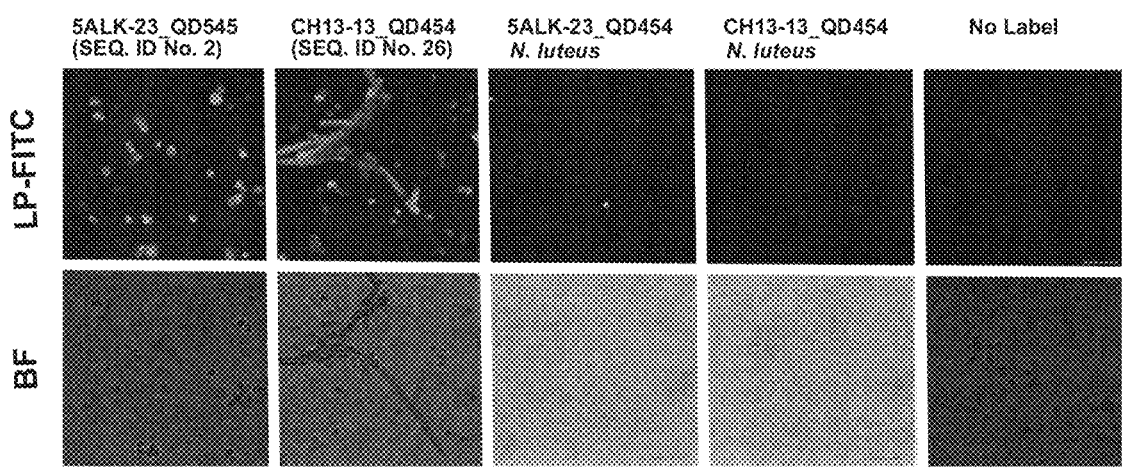
FIG. 6-7 are exemplary fluorescent images of fuel-degrading fungi labelled with SEQ. ID No. 2 and SEQ. ID No. 26 peptides biorecognition elements-conjugated to QD545
Figure 7:
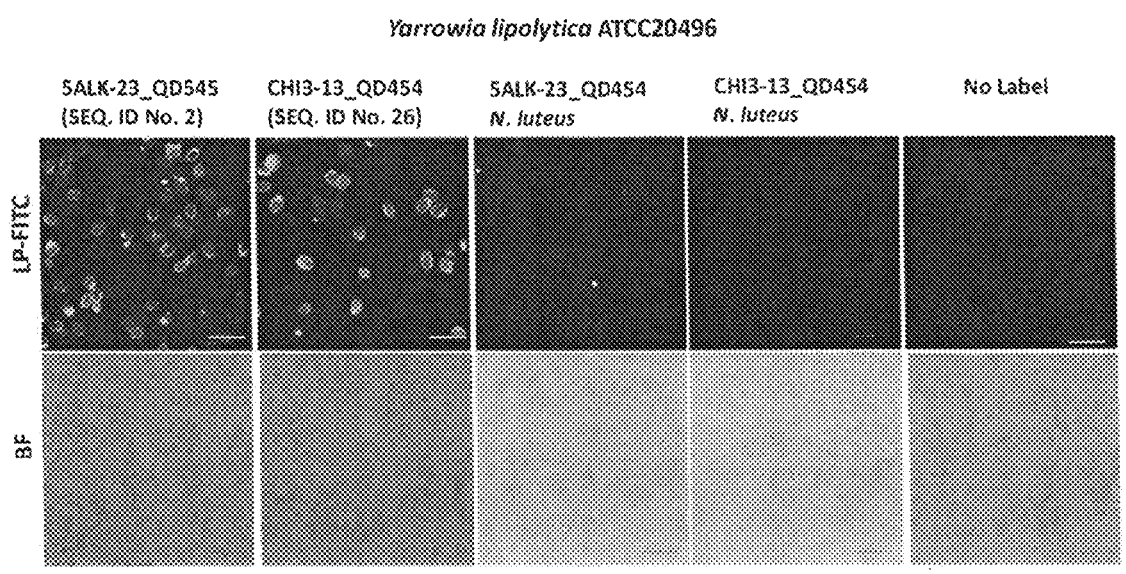
Figure 8:
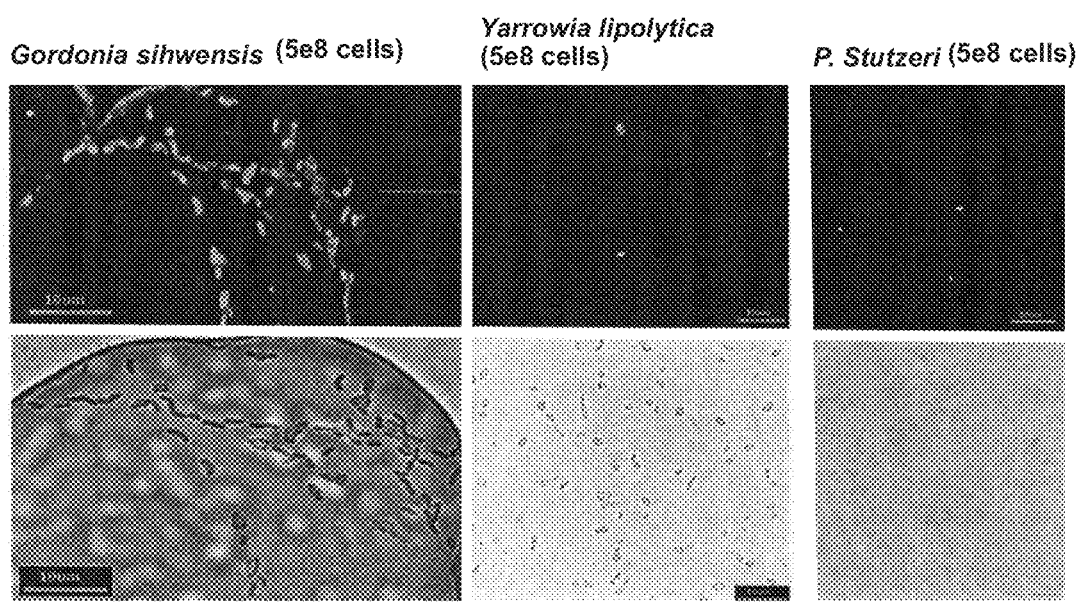
FIGS. 8-9 are exemplary fluorescent images of fuel-degrading Gram-Positive bacteria labelled with SEQ. ID No. 59 and SEQ. ID No. 140 peptides biorecognition elements-conjugated to QD545.
Figure 9:
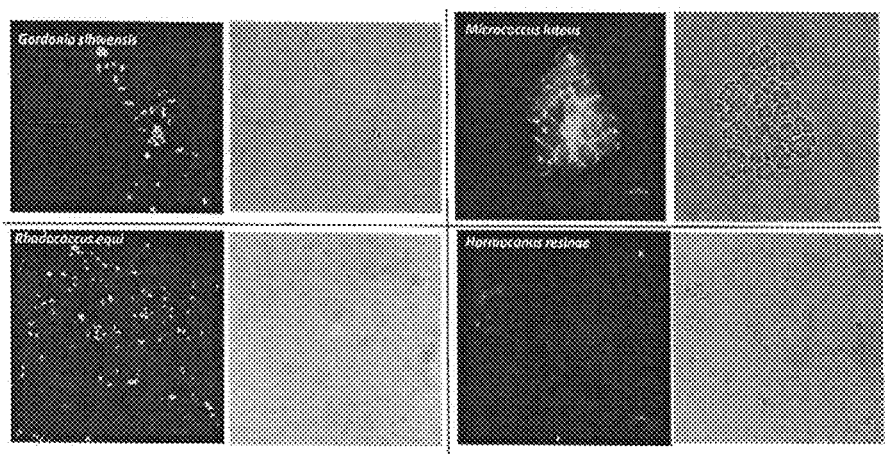
Figure 10:
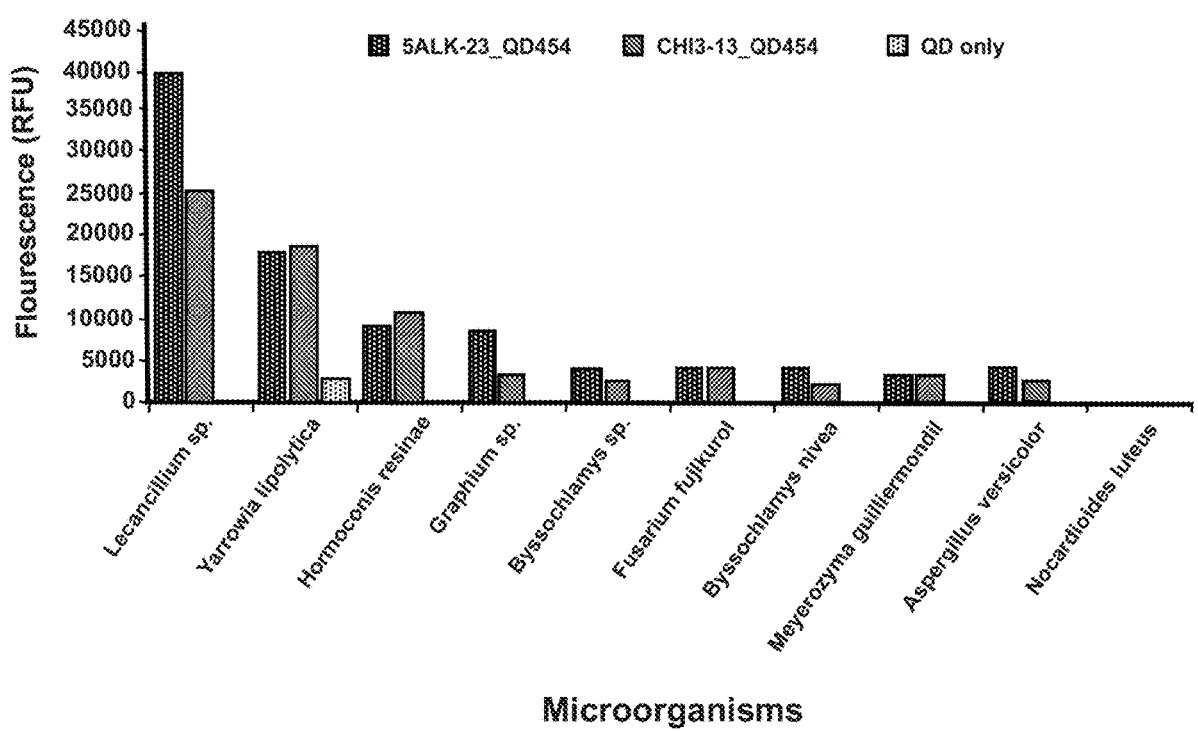
FIG. 10 is graphical representation of fluorescence signal intensity of different fungi labelled with SEQ. ID No. 2 and SEQ. ID No. 26 peptides biorecognition elements-conjugated to QD545
Figure 11:
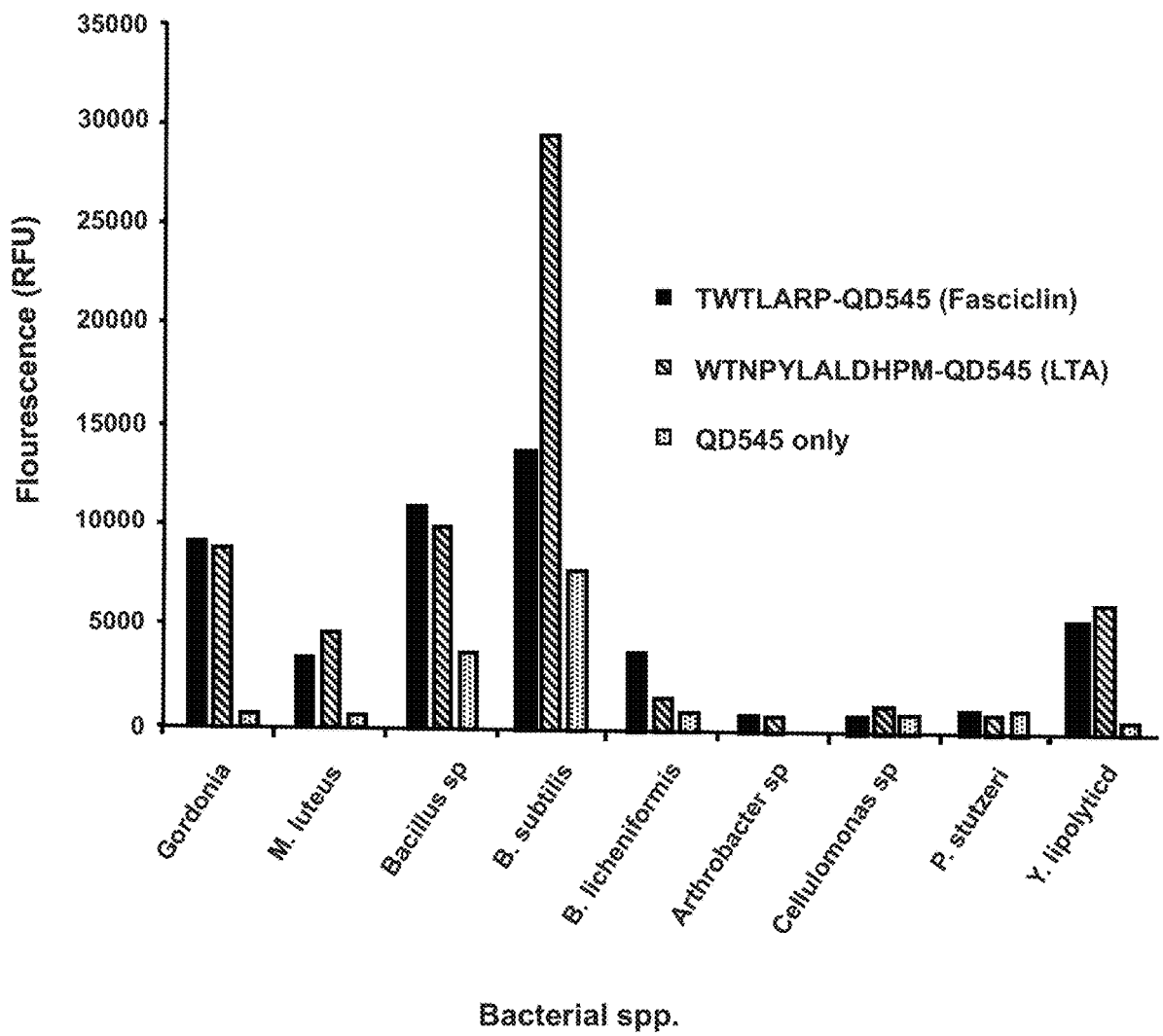
FIG. 11 is graphical representation of fluorescence signal intensity of different Gram-Positive bacteria labelled with SEQ. ID No. 59 and SEQ. ID No. 140 peptides biorecognition elements-conjugated to QD545: P. stutzeri is negative control FIGS. 12-13 Limit of detection of SEQ. ID No. 59 and SEQ. ID No. 140 peptides biorecognition elements targeting Gram-Positive bacteria FIG. 14 Limit of detection of SEQ. ID No. 2 and SEQ. ID No. 26 peptides biorecognition elements-conjugated to QD545 targeting fungi FIG. 15 Relative Fluorescence Unit (RFU) level for $1 \times 10^4$ cells of the filamentous fungus Hormocoins resinae labelled with SEQ. ID No. 2 peptides biorecognition element conjugated to QD545 and QD525.

To characterize the specificity of the peptide BRE-QD545 conjugates for the Gram-positive bacteria and fungi, fluorescence imaging and fluorometric analysis were performed using different Gram-positive bacteria and fungi. As such, cultures comprising $1 \times 10^9$ cells of Gram-positive bacteria (e.g., *Micrococcus luteus, Bacillus subtilis, Gordonia* spp.) were labeled with QD545 biofunctionalized with peptides BREs SEQ. ID No. 59 and SEQ. ID No. 116 and visualized using fluorescence microscopy (FIGS. 8-9) and the fluorescence quantified using a fluorometer (FIG. 11). Similarly various fungi (e.g., *Lecanicillium* sp., *Yarrowia lipolytica*) were labelled QD545 biofunctionalized with peptides BREs SEQ. ID No. 2 and SEQ. ID No. 26 and visualized using fluorescence microscopy (FIGS. 6-7) and the fluorescence quantified using a fluorometer (FIG. 10).

Microbial stocks for experimentation were prepared by harvesting overnight grown bacterial cells by centrifugation at 11000xg for 15 min (at 4° C.), washed once with 1xPBS, pH 7.2, and re-suspended in 1xPBS to a concentration of $1 \times 10^9$ cells/mL. Bacterial titers were determined by measuring optical density at 600 nm and confirmed by colony counting on LB agar plates. Cell pellets produced by centrifuging 1 mL of the $1 \times 10^9$ cells/mL stock were re-suspended in 38 µL of 1xPBS and 62 µL of 2.4 µM peptide-QD was added to a final concentration of 1.5 µM. Cells were incubated for 30 min at 25° C. Cell pellets were washed three-times with 0.5 mL PBS and re-suspended in 500 µL PBS for fluorescence assays and imaging. Dilutions ranging from $1 \times 10^9$ cells to $1 \times 10^4$ cells were prepared using standard bacteriological techniques and 0.5 mL samples were used for fluorescence measurements.

Emission spectra were obtained using Cary Eclipse Fluorimeter with excitation at 330 nm, scan rate of 120 nm/min, and PMT voltage of 1000V. Spectra were corrected for background and dilution factor when appropriate.

10 µL of the prepared sample was placed on a microscope slide, covered with a coverslip, and visualized on an Nikon Eclipse Ti-E inverted microscope equipped with X-Cite LED lamp, a fluorescence filter set (a bandpass exciter 405 nm and a longpass emission filter), a 1.25-numerical-aperture oil-immersion objective (DPlan 100x, Nikon). Images were captured by Nikon DS-sCMOS camera. The fluorescence micrographs showed specific detection of Gram-positive bacteria and fungi by the peptide BREs (FIGS. 6-9. The developed bacterial and fungal BREs were specific and did notcross-reacted with unintended microorganisms.

FIG. 11 shows validation of developed BREs against several Gram-positive bacteria including *Micrococcus luteus, Gordonia* sp., *Bacillus subtilis* and *Bacillus* sp., Very low background fluorescence was observed for non-target Gram-negative bacteria *P. stutzeri*) demonstrating the specificity of the developed peptide BREs.

Example 3

To test the applicability of the peptide BRE-QD chemistry for detection of Gram-positive bacteria and fungi in fuel and characterize the limit of detection (LOD)=, 1 L fuel samples with different concentration of Gram-positive bacterial and =fungal species were tested.

Figure 12:
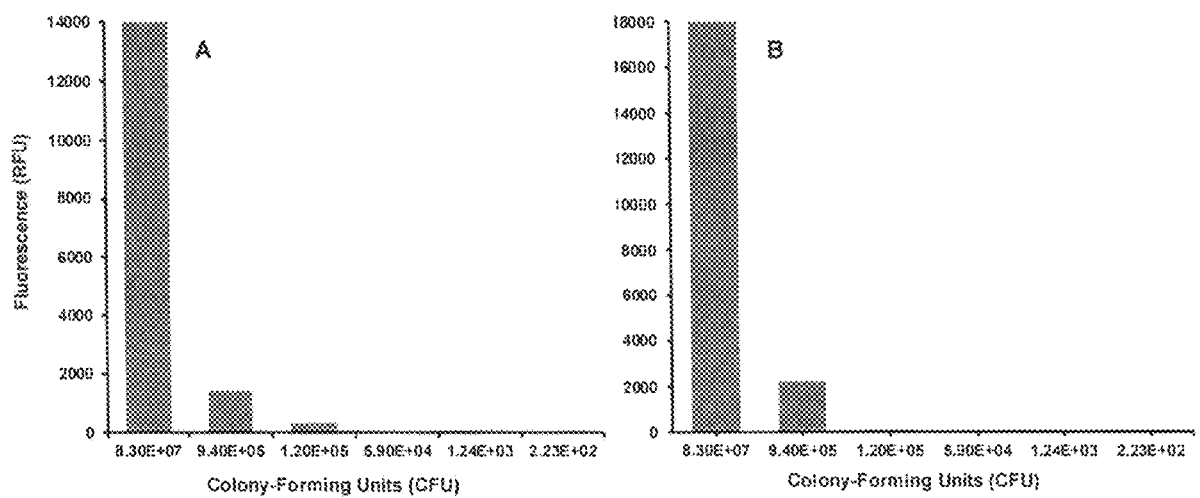
Figure 13:
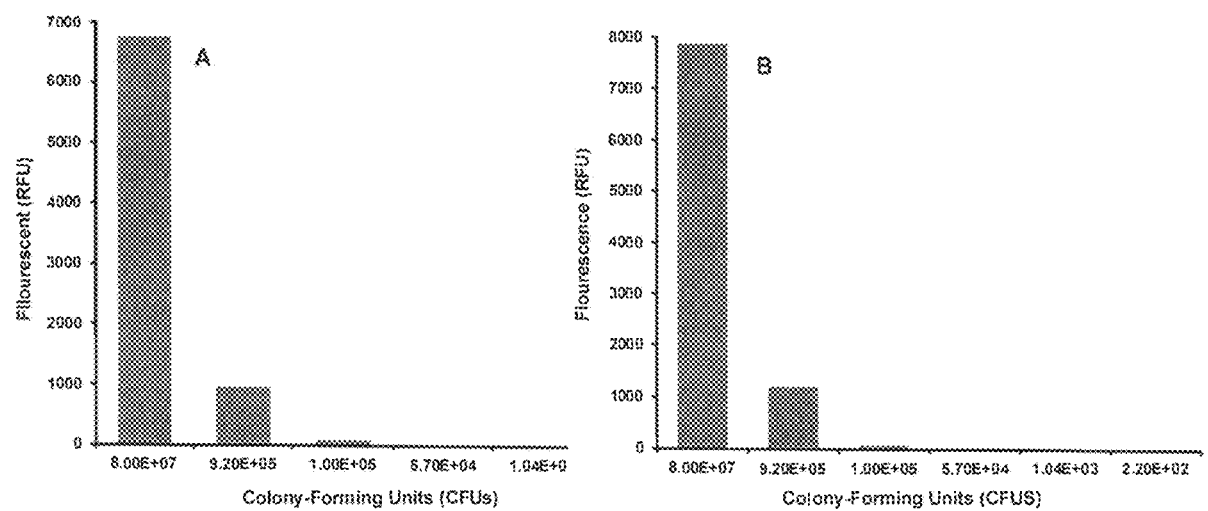
Figure 14:
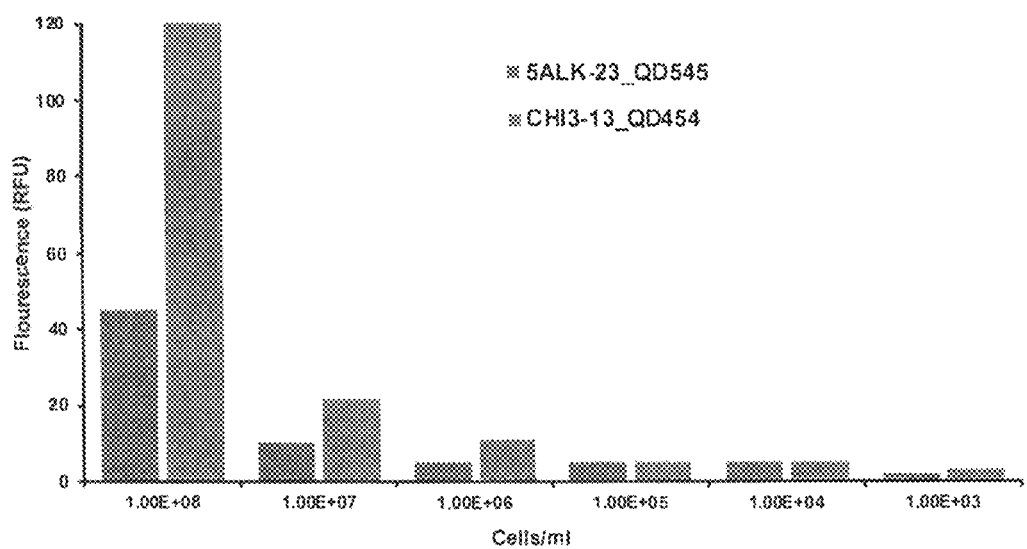

One liter Jet A fuel samples were amended with 1 mL of 1×PBS containing different concentration of Gram-positive bacteria and fungi. The inoculated jet fuel samples were thoroughly mixed and allowed to stand for 20 min. To recover the cells in the fuel, 1 mL of 1×PBS, named bacterial recovery solution ("BRS"), was added to each fuel samples, the samples shaken by hand, allowed stand for 5 min, and then, 1 mL of the aqueous phase was collected using a long serological pipette. The 1 mL of solution with bacteria or fungi was centrifuged for 5 min at 11,000 rpms, and the bacterial or fungal pellets individually labeled using a final concentration 1.5 μM peptide-QD. The LOD was defined as the lowest concentration level that could be determined to be statistically different from QD labeled cells from the results of multiple testers. The actual cell level (colony-forming units, "CFU") detected was determined by plating a portion of the sample after being subjected to the labeled procedure. Efficient labeling of the Gram-positive bacteria (FIGS. 8 & 9) and fungi (FIGS. 6 & 7) was indicated by high levels of fluorescence detected from the cell wall by fluorescence microscopy. The Gram-positive bacteria were detected at an LOD of $9.2 \times 10^5$ CFU/mL to $1.2 \times 10^5$ CFU/mL (FIG. 12 & FIG. 13) and the fungi at an LOD of $1 \times 10^3$ cells/mL (FIG. 14). Lower LOD may be achieved by substituting all centrifugation steps with a single filter membrane to recover cells from the fuel, carryout all washes, and perform the detection step, all of which may prevent the loss of labeled bacteria, reduce background fluorescence, and improve the assay LOD.

Example 4

Figure 15:
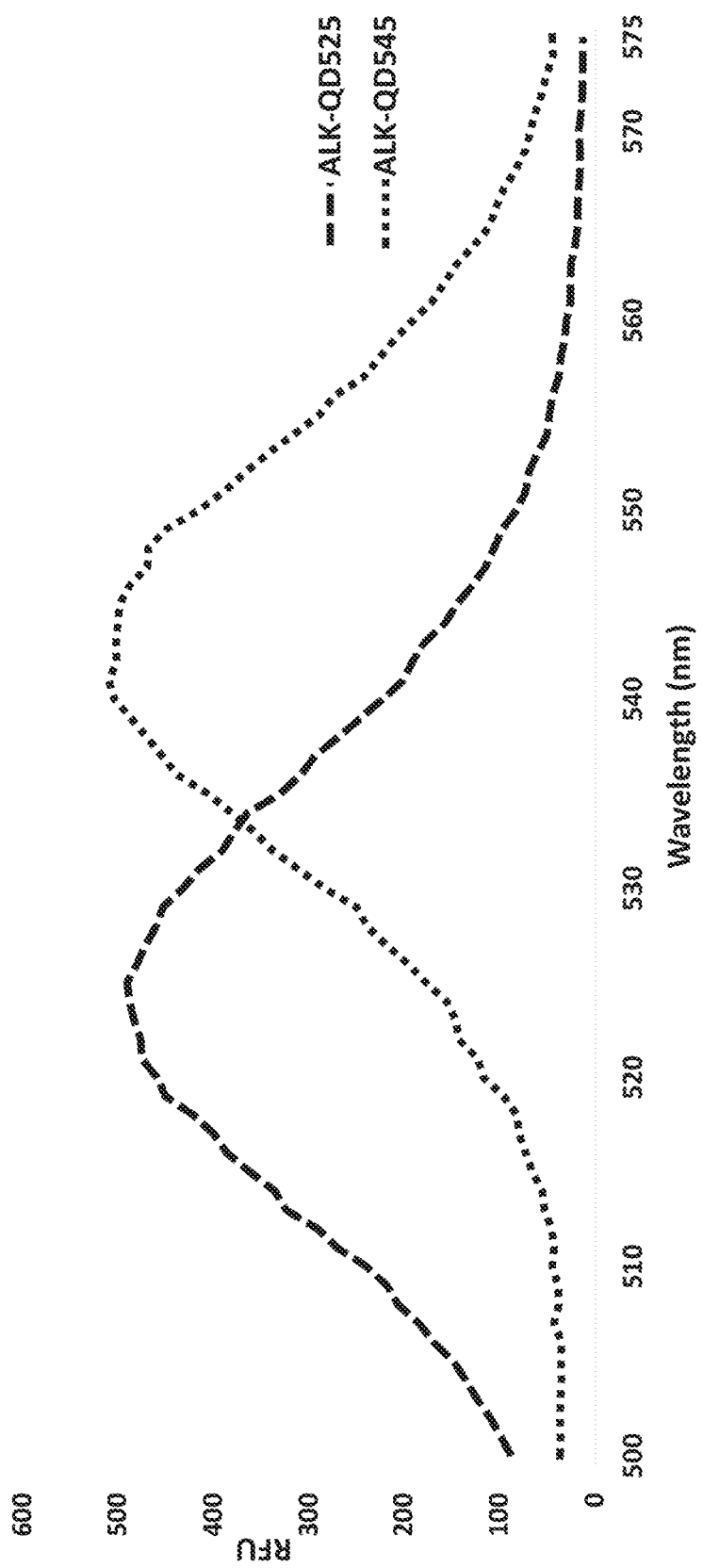

The fluorescence level results shown in FIG. 15 indicate high sensitive of the peptide BRE-QD conjugates against Gram-positive and a filamentous fungus (Hormocoins resinae). FIG. 15 also shows that the peptide BREs described herein can be conjugated to QDs of different emission spectra to allow multiplex detection of bacteria and fungi simultaneously.

Overall, the Colony Forming Units (CFUs) calculated from culture methods correlated well with the high RFU values provided by the peptide BRE-QD assay. This indicated the peptide BRE-QD chemistry and the established test method was suitable for quantification of Gram-positive bacteria and fungi in fuel samples.

The methods described herein according to various embodiments thereof provide certain benefits of conventional methods, including the ability of the BREs described herein to target small biomolecules and epitopes that are conserved among large groups of fuel degrading microorganism and produced during growth in fuel. Additionally, the embodiments of the present invention provide peptide selection methods that were evaluated against changes in temperature, pH, and salt concentration so as to select those BREs that retain binding activity and specificity in the presence of hydrocarbon fuels. These BREs were selected and derived from the fundamental understanding of the adaptive mechanisms and biomolecules used and produced by hydrocarbon-degrading microorganisms during growth in fuel-containing environments. Embodiments of the present invention that include peptide-based devices provide accurate and quantitative real-time detection of microbial growth in fuel in the field (e.g., fuel samples, fuel tanks, pipelines) before high cell density is reached which leads to biofilms formation and biodeterioration.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A biorecognition element, the biorecognition element comprising:
SEQ. ID No. 2, SEQ. ID No. 26, SEQ. ID No. 59, SEQ. ID No. 60, SEQ. ID No. 61, SEQ. ID No. 140, SEQ. ID No. 141 or SEQ. ID No. 142 and a C-terminal, three-glycine plus cysteine linker configured to cross-link to an amine-functionalized quantum dot.

2. The biorecognition element of claim 1, further comprising:
an amine-functionalized quantum dot cross-linked to the cysteine linker; and
a reporter molecule conjugated to the amine-functionalized quantum dot.

3. The biorecognition element of claim 2, wherein the reporter molecule is a fluorescent molecule, a chemiluminescent molecule, a colorimetric molecule, or a signal transducing nanomaterial.

4. A method of detecting biocontamination, the method comprising:
labeling isolating microbes from a fuel sample with a first reporter, wherein the first reporter is conjugated to a biorecognition element comprising: SEQ. ID No. 2, SEQ. ID No. 26, SEQ. ID No. 59, SEQ. ID No. 60, SEQ. ID No. 61, SEQ. ID No. 140, SEQ. ID No. 141 or SEQ. ID No. 142 and a C-terminal, three-glycine plus cysteine linker configured to cross-link to an amine-functionalized quantum dot.

5. The method of claim 4, wherein the sample is a fuel sample and the method of isolating the isolated microbes comprises:
moving microbes from a fuel phase of the fuel sample to an aqueous phase of the fuel sample;
drawing the aqueous phase from fuel phase; and
obtaining a microbe pellet by centrifugation.

6. The method of claim 4, wherein isolating microbes from the fuel sample comprises:
filtering the microbes from a fuel phase of the fuel sample, an aqueous phase of the fuel sample, or both.

7. The method of claim 4, wherein the reporter is conjugated to the amine-functionalized quantum dot.

8. The method of claim 4, wherein the first reporter is a fluorescent molecule, a chemiluminescent molecule, a colorimetric molecule, or a signal transducing nanomaterial.

9. The method of claim 4, further comprising:
labeling the microbes with a second reporter, wherein the second reporter is conjugated to said biorecognition element.

10. A biocontamination assay kit comprising:
a biorecognition element selected from the group consisting of: SEQ. ID No. 2, SEQ. ID No. 26, SEQ. ID No. 59, SEQ. ID No. 60, SEQ. ID No. 61, SEQ. ID No. 140, SEQ. ID No. 141 and SEQ. ID No. 142;
a C-terminal, three-glycine plus cysteine linker on the biorecognition element;
an amine-functionalized quantum dot cross-linked to the cysteine linker; and
a reporter molecule conjugated to the amine-functionalized quantum dot.

11. The biocontamination assay kit of claim 10, further comprising:
a filter permeable to liquid and configured to retain microbes.

12. The biocontamination assay kit of claim 11, wherein the liquid is a fuel.

13. The biocontamination assay kit of claim 10, wherein the reporter molecule is a fluorescent molecule, a chemiluminescent molecule, a colorimetric molecule, or a signal transducing nanomaterial.

* * * * *